(12) United States Patent
Clark

(10) Patent No.: US 7,018,203 B2
(45) Date of Patent: Mar. 28, 2006

(54) MANDIBULAR ADVANCER AND METHOD OF INSTALLING THE SAME

(76) Inventor: William J. Clark, Lundin Lea, Leven Rd, Lundin Links, Fife KY8 6AJ, Scotland (GB)

( * ) Notice: Subject to any disclaimer, the term of this patent is extended or adjusted under 35 U.S.C. 154(b) by 0 days.

(21) Appl. No.: 10/117,986

(22) Filed: Apr. 8, 2002

(65) Prior Publication Data

US 2003/0031976 A1   Feb. 13, 2003

Related U.S. Application Data

(63) Continuation of application No. 09/648,086, filed on Aug. 25, 2000, now Pat. No. 6,368,106, which is a continuation-in-part of application No. 09/559,792, filed on Apr. 27, 2000, now abandoned, which is a continuation-in-part of application No. 09/533,892, filed on Mar. 22, 2000, now abandoned.

(51) Int. Cl.
*A61C 3/00* (2006.01)

(52) U.S. Cl. ........................................................ 433/19
(58) Field of Classification Search .................... 433/6, 433/7, 18, 19, 23, 24, 197, 218, 219
See application file for complete search history.

(56) References Cited

U.S. PATENT DOCUMENTS

| | | | |
|---|---|---|---|
| 4,509,918 A | 4/1985 | Clark | 433/5 |
| 5,443,384 A | 8/1995 | Franseen et al. | 433/18 |
| 5,683,244 A | 11/1997 | Truax | 433/6 |
| 5,848,891 A | 12/1998 | Eckhart et al. | 433/19 |
| 5,871,350 A | 2/1999 | Clark et al. | 433/18 |
| 6,099,304 A | 8/2000 | Carter | 433/19 |

*Primary Examiner*—Cary E. O'Connor
(74) *Attorney, Agent, or Firm*—Marsh Fischmann & Breyfogle LLP

(57) ABSTRACT

Multiple embodiments of mandibular advancers are disclosed. Advancement of the mandible is affected by mounting such an mandibular advancer on each side of both the upper dental arch and the lower dental arch. One embodiment of such an mandibular advancer includes a casting form with a rigid polymerized material therein and which includes a casting form mandibular advancement incline formed on an end thereof. The casting form mandibular advancement incline may wear away in certain instances to expose the polymerized material therebeneath which has been cured and assumed the shape of this casting form mandibular advancement incline. Other embodiments of such mandibular advancers include a crown or a band, each of which has a mandibular advancement incline as a part thereof (e.g., integrally, via separate attachment). Certain of these crowns or the band with a mandibular advancement incline associated therewith may be disposed within the above-noted casting form and encapsulated within the noted polymerized material. Preferably this disposes the mandibular advancement incline associated with the crown/band in interfacing relation with the casting form mandibular advancement incline.

29 Claims, 19 Drawing Sheets

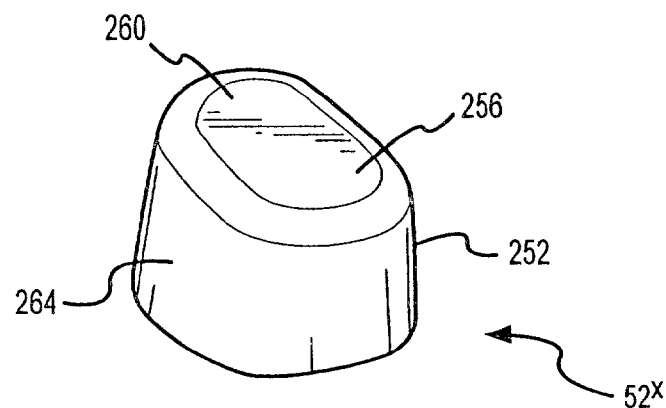
FIG.19
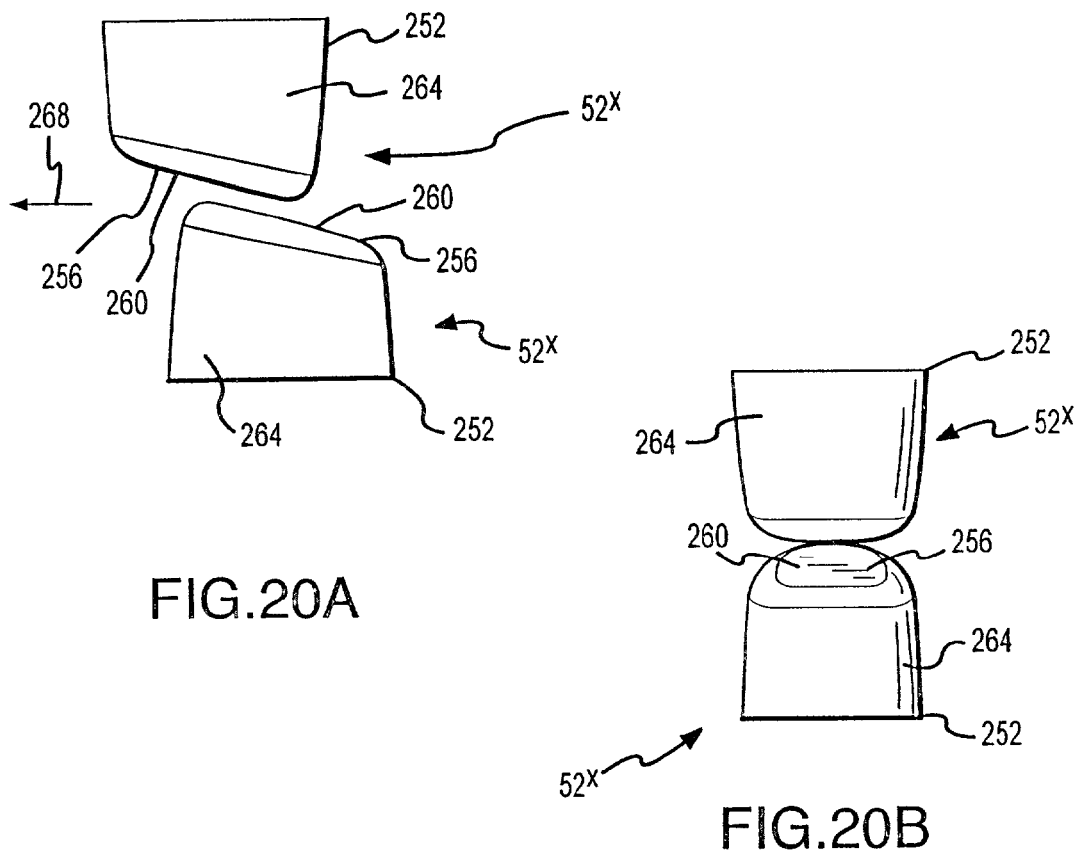
FIG.20A
FIG.20B

MANDIBULAR ADVANCER AND METHOD OF INSTALLING THE SAME

CROSS-REFERENCE TO RELATED APPLICATIONS

This patent application claims priority from and is a continuation of U.S. patent application Ser. No. 09/648,086, which is entitled "MANDIBULAR ADVANCER AND METHOD OF INSTALLING THE SAME," which was filed on Aug. 25, 2000, and now U.S. Pat. No. 6,368,106, which claims priority from and is a continuation-in-part of U.S. patent application Ser. No. 09/559,792, which is entitled "MANDIBULAR ADVANCER AND METHOD OF INSTALLING THE SAME," and which was filed on Apr. 27, 2000 (abandoned), which claims priority from and is a continuation-in-part of U.S. patent application Ser. No. 09/533,892, which is entitled "MANDIBULAR ADVANCER AND METHOD FOR ASSEMBLING THE SAME," and which was filed on Mar. 22, 2000 (abandoned). Priorty is being claimed to each of the noted applications.

FIELD OF THE INVENTION

The present invention generally relates to the field of the advancement of the mandible or lower jaw in typically an orthodontic treatment setting (e.g., to treat an orthodontic patient with a Class II malocclusion, to treat an orthodontic patient with a Class III malocclusion) and, more particularly, to various mandibular advancement devices which include a mandibular advancement incline for affecting mandibular advancement and which may be fixedly attached to one or more teeth of the patient.

BACKGROUND OF THE INVENTION

Class II malocclusions exist when an individual's upper jaw or maxilla protrudes further out from the individual's face than his/her lower jaw or mandible. Conversely, Class III malocclusions exist when an individual's lower jaw or mandible protrudes further out from the individual's face than his/her upper jaw or maxilla. Treatment of a Class II malocclusion may entail exerting a functional orthopedic force on the individual's lower jaw or mandible so as to advance the same in a mesial or "outward" direction.

One way in which orthodontic treatment forces have been applied to address a Class II malocclusion is through a facebow to retract the upper jaw or maxilla to match the position of a retruded mandible. As 70% of Class II malocclusions are due to a deficient mandible, it is more beneficial to the patient to advance the mandible than to retract the maxilla. This results in a better profile, and a more balanced facial appearance, compared to orthodontic techniques which retract the maxillary teeth to match the position of a retrusive mandible. The disadvantage of this approach is that the nose continues to grow, when the maxilla is retracted, and the nose becomes unduly prominent in the profile, while the maxilla and mandible are retracted to a retrusive position. This approach may align the anterior teeth, but at the same time, is detrimental to the patient's facial appearance. The alternative to a functional orthopedic approach to correct a mandibular retrusion would entail a combination of orthodontic and surgical correction to align the teeth and advance the mandible to match the correctly positioned maxilla. Orthopedic correction achieves a similar result by correcting the mandibular position without surgery in many cases. It is important to integrate orthopedic techniques with conventional orthodontic techniques, to allow the simultaneous correction of skeletal and dental abnormalities.

Another option which has been utilized to affect mesially-directed mandibular advancement is through what has been characterized in the orthodontic industry as "bite blocks." Bite blocks generally include a planar surface which is disposed at an angle relative to an individual's occlusal plane when the bite blocks are installed on the patient. Typically a pair of bite blocks are installed on the occlusal surface of the patient's upper dental arch on opposite sides thereof (i.e., one on the right side of the upper dental arch, and another on the left side of the upper dental arch), while a pair of bite blocks are also installed on the occlusal surface of the patient's lower dental arch on opposite sides thereof (i.e., one on the right side of the lower dental arch, and another on the left side of the lower dental arch). Each of these bite blocks are installed so that there is a camming-like action between the two bite blocks which are occlusally installed on the patient's upper arch and their corresponding bite blocks which are occlusally installed on the patient's lower arch.

Both fixed and removable attachment techniques have been suggested for bite blocks generally of the above-noted type. "Fixed" in the orthodontic treatment sense and also as used herein means that a particular appliance is installed on the orthodontic patient in such a manner so that at least in theory the orthodontic patient will not be able to readily remove the appliance, but so that the appliance may be removed by the orthodontic practitioner utilizing the proper tool(s). "Removable" in the orthodontic treatment sense and also as used herein means that a particular appliance is installed on the orthodontic patient in such a manner so that the appliance may be readily removed by both the orthodontic patient and practitioner.

Since the beginning of the twentieth century, orthopedic appliances have traditionally been removable by the patient, therefore being dependent on patient cooperation to achieve the beneficial effects of treatment. The improvements of the present invention addressed below adapt the principles of orthopedic correction, already proven in removable appliance techniques, to fixed orthopedic appliances, thus allowing better control, and better results to be achieved by the unrestricted full time wear of orthopedic appliances.

BRIEF SUMMARY OF THE INVENTION

The present invention generally relates to the advancement of the mandible in typically an orthodontic treatment setting and, more particularly, to the manner in which one or more components used to affect mandibular advancement are assembled for installation on a patient. Both mesial advancement (i.e., treatment of Class II malocclusions) and distal advancement or retraction (i.e., treatment of Class III malocclusions) of the mandible may be affected utilizing principles of the present invention. Nomenclature which will be used herein to describe the various aspects of the present invention defines the corresponding structure/step in relation to the "installed" position or to the position which is assumed within the patient's mouth, and further conforms to the way in which such terms are commonly used in the dental or orthodontic practice to describe particular surfaces of the teeth and orthodontic appliances used in combination therewith and/or orientations relating thereto.

A first aspect of the present invention is a mandibular advancement system which includes a casting form. Multiple options are provided in relation to the particular manner in which a mandibular advancement incline surface is mounted within a patient's mouth through use of this particular casting form. The casting form of this first aspect includes a casting form occlusal surface (e.g., on the "occlusal" side of the casting for when in the patient's mouth), a casting for buccal surface (e.g., on the "buccal" side of the casting form when in the patient's mouth), a casting form lingual surface (e.g., on the "lingual" side of the casting form when in the patient's mouth), and a casting form mandibular advancement incline for at least facilitating mandibular advancement. Typically the casting form mandibular advancement incline will be disposed on either the mesial or distal end of the casting form. One of these casting forms may be installed on one or both sides of the patient's upper dental arch, on one or both sides of an patient's lower dental arch, or on one or both sides of both of the patient's upper and lower dental arches. These various options will be discussed in more detail below, as well as the various ways in which the installation may be affected.

The casting form occlusal, buccal, and lingual surfaces, as well as the mandibular advancement incline, collectively define a hollow repository of sorts (e.g., a hollow, three-dimensional generally wedge-shaped structure). Disposed within this repository of the casting form is a material which has been polymerized to provide a desired degree of rigidity thereto. Typically this material will be provided to the casting form in somewhat of a "fluid" or "flowable" state (e.g., a paste), such that one could think of the casting form as a "bathtub" or trough of sorts for retaining this fluid-like or flowable material therein for subsequent polymerization. In any case, the casting form is installed on the desired side of the desired dental arch of the patient such that this now polymerized material at least projects toward at least the occlusal surface of at least two or more teeth in the corresponding dental arch (e.g., the polymerized material may extend along the buccal and/or lingual sides of the noted teeth as well). An appropriate chemically polymerizing orthodontic bonding system (e.g., a primer and paste, a paste-paste, a photo-initiated orthodontic bonding system) may be applied to those surfaces of the polymerized material which will interface with the corresponding dental arch, or the curing of the flowable material on the patient's teeth may itself establish the bond between the polymerizable material and the teeth (e.g., using traditional/customary orthodontic composite resins for the flowable material and to define the polymerized material when cured).

The casting form's mandibular advancement incline is positioned on the casting form relative to this polymerized material so that when the casting form is installed in the above-noted manner, the casting form mandibular advancement incline is disposed at an angle relative to the occlusal plane of the corresponding dental arch, and further preferably extends at least substantially perpendicularly across the major axis of the dental arch. Engagement of this casting form mandibular advancement incline (or the preferably conformingly-shaped underlying structure if the casting form material which forms the casting form mandibular advancement incline has worn away) by appropriate structure on the opposing dental arch (e.g., another mandibular advancer installed on the same side of the opposing dental arch and with a generally oppositely oriented mandibular advancement incline) may be used to at least facilitate advancement of the mandible in the mesial or the distal direction by the noted camming-like action.

Various refinements exist of the features noted in relation to the subject first aspect of the present invention. Further features may also be incorporated in the subject first aspect of the present invention as well. These refinements and additional features may exist individually or in any combination. The casting form occlusal surface may be contoured for various purposes. That portion of the casting form occlusal surface which extends distally or mesially of the mandibular advancement incline (as the case may be depending upon, for instance, the type of malocclusion being treated and/or whether the casting form is for the upper or lower arch), may be a substantially planar surface and further may be disposed at least substantially parallel with the occlusal plane of the dental arch on which the casting form is installed. Preferably the mesio-distal extent of this particular surface is at least as great as the mesio-distal extent of the tooth within the dental arch which underlies this surface. Configuring at least this portion of the casting form occlusal surface in this manner provides a surface on which a mandibular advancer on the opposing dental arch may engage the casting form occlusal surface of the casting form associated with this first aspect to slide thereon, through a mesially or distally directed movement of the mandible by the patient, so as to position the opposing mandibular advancement incline for engagement with the casting form mandibular advancement incline associated with this first aspect or underlying structure as noted above.

All of the casting form occlusal surface need not have the same profile. For instance, in the case where that portion of the casting form occlusal surface which extends from the casting form mandibular advancement incline is disposed at least generally parallel with the occlusal plane of the dental arch on which the casting form is installed (e.g., a first section of the casting form occlusal surface), the remainder of the casting form occlusal surface (e.g., a second section), may extend away from this first section not in parallel relation with the corresponding occlusal plane, but instead at least generally toward the patient's gingiva which is associated with the dental arch on which the casting form is installed. Stated another way, the second section of the casting form occlusal surface may slant toward the dental arch on which the casting form is installed.

All or at least a portion of the casting form occlusal surface may be contoured to account for orthodontic conditions other than a Class II or III malocclusion. For instance, all or part of the casting form occlusal surface may be recessed a certain degree to account for what is known as a "deep bite" orthodontic condition (e.g., to present a concave surface). In addition, all or part of the casting form occlusal surface may be bulged a certain degree or the casting form may have an enhanced occlusal-gingival extent to account for what is known as an "open bite" orthodontic condition.

The distance between the casting form buccal and lingual surfaces, or the "width" of the casting form, may be selected to be at least slightly greater than the distance between the buccal and lingual surfaces of the dental arch on which the casting form is to be installed. In this case the casting form will extend along a portion of the buccal and/or lingual surfaces of the subject dental arch when installed thereon, as well as along a portion of the subject dental arch's occlusal surface. Polymerized material may thereby extend along these buccal and/or lingual surfaces of the subject dental arch as well to provide a more robust interconnection of the mandibular advancement system with the subject dental arch.

The occlusal-gingival extent of the casting form buccal and lingual surfaces need not be equal in relation to the first aspect of the present invention. Materials may be used to make the casting form which will allow the orthodontic practitioner, or more typically personnel associated with an orthodontic laboratory, to trim the casting form to the desired degree prior to the disposal of the polymerizable material therein. For instance, the occlusal-gingival extent of the casting form lingual surface may be greater than the occlusal-gingival extent of the casting form buccal surface, or vice versa. One advantage of having the enhanced occlusal-gingival extent on the casting form lingual surface is that the casting form and polymerized material may encapsulate certain orthodontic armamentarium disposed on the lingual surface of the subject dental arch (e.g., lingual arches) to provide a more robust interconnection of the casting form with the corresponding dental arch. In other cases it may be desirable for the casting form lingual and/or buccal surface to have a reduced occlusal-gingival extent over certain portions thereof so as to not interfere with orthodontic armamentarium disposed on the lingual and/or buccal surface of the subject dental arch. Relatedly, the occlusal-gingival extent of the casting form buccal and/or lingual surfaces need not be the same throughout the entire mesio-distal extent or "length" of the casting form. For instance, that mesio-distal section of the casting form buccal and/or lingual surfaces which is disposed adjacent to and/or extends mesio-distally from the casting form mandibular advancement incline may have an enhanced occlusal-gingival extent compared to another mesio-distal section of the casting form buccal and/or lingual surfaces which is disposed further from that end of the casting form which includes the casting form mandibular advancement incline. This may be desirable for purposes of secure retention by engaging the buccal or lingual surfaces of the underlying teeth.

The casting form of the subject first aspect may include structure which extends from a gingival-most edge of the casting form mandibular advancement incline, and in the direction of the dental arch on which the casting form is installed. In one embodiment this "extension" may be characterized as having an at least generally u-shaped profile so as to at least generally approximate that portion of the dental arch over which the extension is disposed. Typically the casting form will be positioned on the subject dental arch so that this extension is disposed interproximally between two adjacent teeth within the subject dental arch. The occlusal-gingival extent of this extension may be greater than the occlusal-gingival extent of the casting form buccal and/or lingual surfaces for purposes of contouring the appliance to engage the supporting teeth, or as a means of attachment to a lingual arch which may be disposed to control the transverse dimension simultaneously with the mandibular advancement. In other cases the noted extension may have the same occlusal-gingival extent as adjacent portions of the casting form lingual and/or buccal surfaces.

As noted above, the material from which the casting form of the subject first aspect of the present invention is made is preferably that which will allow an orthodontic practitioner or orthodontic laboratory technician to readily trim the casting form to the desired shape for a given patient. Moreover, preferably the material from which the casting form is made will further cross-link with the polymerizable material disposed therein to further enhance the interconnection between the casting form and this polymerizable material.

Significant flexibility is provided by the casting form associated with the subject first aspect in relation to how the mandibular advancement system is actually installed on the patient. In one embodiment, the casting form with the polymerized material therein may provide the entirety of one mandibular advancer of the mandibular advancement system of the first aspect. A suitable orthodontic bonding system may be applied in this case to those portions of the polymerized material within the casting form which will project toward the subject dental arch (when the casting form/polymerized material is initially formed on a stone casting and as will be discussed in more detail below), or the polymerizable material may be allowed to cure while on the teeth, all such that the casting form and polymerized material may be fixedly bonded directly to the subject dental arch. Another option is to use the casting form associated with the subject first aspect in combination with a crown as a mandibular advancer of the mandibular advancement system of the first aspect. Generally, this crown may be disposed within the "hollow" of the casting form and be securely retained therein by the polymerized material. In this case not only would portions of the polymerized material within the casting form be directly fixedly bonded to the subject dental arch, but the crown would also be disposed over a tooth within this particular dental arch and be fixedly bonded thereto.

One embodiment of a combination casting form/crown mandibular advancer utilizes a crown assembly. This crown assembly may be disposed within the casting form of the subject first aspect and includes a crown with a crown occlusal surface which "overlies" a single tooth of the dental arch on which the mandibular advancement system of the first aspect is installed, as well as an annular crown skirt which is disposed about this particular tooth. A crown mandibular advancement incline frame is separately attached to this particular crown. Stated another way, the crown mandibular advancement incline frame and crown in this case are separate parts, and are thereby not formed from a single piece of material (i.e., there is at least one joint therebetween). This particular crown mandibular advancement incline frame includes first and second frame sections which are configured such that there is an acute angle therebetween. The first frame section is disposed on and is appropriately attached to the crown occlusal surface of the crown (e.g., via one or more spot welds, via brazing) so that the second frame section extends away from both the first frame section and the crown occlusal surface of the crown. The second frame section may therefore be characterized as a crown mandibular advancement incline, and such may be a flat, planar surface. In one embodiment, the first frame section extends beyond the crown occlusal surface such that the second frame section is disposed at an interproximal location between two teeth within the dental arch on which the mandibular advancement system of the first aspect is installed. In any case, the first frame section is mounted on the crown occlusal surface of the crown such that the second frame section is disposed at least generally proximate to and at least generally parallel with the casting form mandibular advancement incline. Preferably the second frame section and casting form mandibular advancement incline are disposed in interfacing relation. In this case, polymerized material will typically occupy the entirety of the space between the crown occlusal surface of the crown and the casting form occlusal surface.

Attachment of the first frame section to the crown occlusal surface of the crown may be facilitated by having the crown occlusal surface be at least substantially planar. Conventional crowns include an occlusal surface which is contoured to at least generally replicate the occlusal surface of a tooth, and thereby the crown which is associated with the mandibular advancement system of the first aspect of the present invention in this instance is a significant departure from these conventional crowns. Enhancement of the interconnection between the crown and the crown mandibular advancement incline frame may be realized by incorporating at least one, and more preferably a plurality of, apertures which each extend through the entire occlusal-gingival extent of the first frame section. At least one of these apertures may be disposed so as to expose a portion of the crown occlusal surface on which the first frame section overlies. Polymerized material may occupy the entire extent of any such apertures. At least one aperture may also be disposed on that portion of the first frame section which extends beyond the crown occlusal surface of the crown. This may facilitate the directing of polymerizable material within the space defined between the first and second frame sections. Polymerizable material may be captured within this space between the first and second frame sections by having a pair of extensions which project from the opposite sides of the first frame section at least toward the "free" end of the second frame section or at least an apex thereof (e.g., a pair of triangularly-shaped "ears").

Another crown which may be used in combination with the casting form to define a mandibular advancer of the mandibular advancement system of the subject first aspect includes an integral crown mandibular advancement incline which may be a flat, planar surface or alternatively which may have a curvature about a reference axis which is at least generally parallel with a tooth-long axis of a tooth on which the crown is installed (e.g., defined by rotating a line about such an axis). That is, the crown occlusal surface, annular crown skirt, and crown mandibular advancement incline are formed from a single piece of material in this case and thereby with no joint of any kind therebetween. This crown mandibular advancement incline is disposed on the crown so as to be disposed at least generally proximate to and at least generally parallel with the casting form mandibular advancement incline when the casting form and crown are installed on one side of the desired dental arch. Preferably, the crown mandibular advancement incline and casting form mandibular advancement incline are disposed in interfacing relation.

In one embodiment, the above-noted crown mandibular advancement incline is disposed on a mesial or distal end of the crown. This could be viewed as being at a location where the crown occlusal surface and skirt would otherwise intersect. In another embodiment, the crown mandibular advancement incline is formed into a "mid" or "interior" portion of the crown occlusal surface. Stated another way, the crown mandibular advancement incline may be disposed somewhere between the mesial and distal extremes of the crown. For instance, the crown occlusal surface may include first and second sections which are disposed at different elevations (i.e., one being "raised" relative to the other) and the crown mandibular advancement incline may be disposed therebetween. In yet another embodiment, the crown mandibular advancement incline may define at least substantially the entirety of the crown occlusal surface of the crown. In this case, the crown mandibular advancement incline may be oriented so as to be disposed at an angle of no more than about 20° relative to a plane which is parallel with the occlusal plane of the dental arch on which this particular crown is installed.

Regardless of the positioning of the crown mandibular advancement incline on the above-noted integrally formed crown, the crown may have an increased occlusal-gingival extent in relation to conventional crowns. In this regard and in one embodiment, there is at least about a 1.5 mm minimum space between the apex of the crown occlusal surface and the occlusal-most surface of the tooth over which the crown is disposed to allow for the incorporation of the crown mandibular advancement incline integrally with the crown. This space may remain hollow or may be filled with polymerizable material to enhance the rigidity of the crown mandibular advancement incline.

Another variation of a crown which may be used in combination with the casting form to define a mandibular advancer of the mandibular advancement system of the subject first aspect includes an extension which projects away from the annular crown skirt. The crown mandibular advancement incline in this case is thereby disposed beyond the "oval" of the crown on the "free" end of this extension (e.g., at the end of this cantilever). Stated another way, the crown mandibular advancement incline in this case is disposed on an end of the extension which is opposite that which interfaces with the crown skirt. Extensions which are integrally formed with the crown (i.e., formed from the same piece of material and with no joint of any kind therebetween, such as by a hydroforming process), as well as an extension which is separately formed from the crown and thereafter separately attached thereto, are contemplated. This particular embodiment may be effective at the more advanced stages of the treatment of a Class II or III malocclusion by moving the activating surface (e.g., the crown mandibular advancement incline) more mesially or distally to account for that amount of mesial or distal movement of the mandible which has already been achieved, as the case may be. In any case, the crown mandibular advancement incline is preferably a flat, planar surface.

Conventional orthodontic bands may also be used in combination with the above-described casting form to define a mandibular advancer of the mandibular advancement system of the subject first aspect. Generally, this band may be disposed within the "hollow" of the casting form and be securely retained therein by the polymerized material. In this case not only would portions of the polymerized material within the casting form be directly bonded to the subject dental arch, but the orthodontic band would also be disposed about a tooth within this particular dental arch and then bonded thereto. A band mandibular advancement incline frame is associated with this band. One embodiment entails attaching this band mandibular advancement incline frame to both the occlusal and buccal surfaces of the band. In any case, the band mandibular advancement incline frame is oriented on the band so that its band mandibular advancement incline, which is disposed on the free end thereof, is disposed at least generally proximate to and a least generally parallel with the casting form mandibular advancement incline when the casting form and band are installed on one side of the desired dental arch. Preferably, the band mandibular advancement incline and casting form mandibular advancement incline are disposed in interfacing relation. In one embodiment, the band mandibular advancement incline frame is encapsulated within the polymerized material, which again is retained within and preferably cross-linked with the casting form. Moreover, preferably the band mandibular advancement incline is a flat, planar surface.

A second aspect of the present invention is directed to a method for assembling a mandibular advancement system (e.g., of the type described with regard to the first aspect) for use by a patient. The method includes the steps of disposing a polymerizable material within a casting form which includes a casting form mandibular advancement incline disposed on typically a mesial or distal end thereof. The casting form with the polymerizable material therein is thereafter disposed in overlying relation to least part of at least two tooth-like structures which are associated with a certain dental arch of a patient. The term "at least two tooth-like structures" means that this step may be affected on a stone casting which has been previously made of the subject dental arch, and which are thereby not the patient's actual teeth, as well as directly on the patient's teeth. The casting form is more particularly positioned on at least the occlusal surface of the noted "structures" and the polymerizable material is cured into an at least substantially rigid form so that the casting form mandibular advancement incline is disposed in a proper position. This "proper position" is one where the casting form mandibular advancement incline is disposed at an angle relative to an occlusal plane of the dental arch on which the casting form with polymerized material therein is ultimately installed within the patient's mouth. Disposing the casting form mandibular advancement incline at this angle facilitates the provision of an "activating" surface for affecting mandibular advancement.

Various refinements exist of the features noted in relation to the subject second aspect of the present invention. Further features may also-be incorporated in the subject second aspect of the present invention as well. These refinements and additional features may exist individually or in any combination. One way to assemble the mandibular advancement system associated with the second aspect is in an orthodontic laboratory environment or the like. In this case, a stone casting is made of the dental arch on which the mandibular advancement system which is associated with the second aspect is to be installed. An appropriate release agent is typically applied to relevant portions of this stone casting. Thereafter, the casting form with the polymerizable material therein is positioned on the stone casting at the desired locale. The polymerizable material interfaces with at least the occlusal surface of the dental arch which is replicated by the stone casting, and possibly its buccal and/or lingual surfaces as well (e. g., the casting form may extend along at least a portion of the buccal and/or lingual surfaces of the subject dental arch, as well as along part of its occlusal surface). After the polymerizable material has had a chance to at least partially cure while on the stone casting (e.g., so as to retain the shape of the polymerizable material when removed from the stone casting), the casting form with the at least partially cured polymerizable material therein is removed from the stone casting. Typically the casting form with the at least partially cured polymerizable material will then be disposed within an appropriate oven or the like to complete the curing cf the polymerizable material to the desired degree of rigidity. Installation of this casting form and the now polymerized material on the corresponding side of the corresponding dental arch of the patient is then affected "chairside" by the orthodontic practitioner applying an appropriate orthodontic bonding system to least part of the rigid polymerized material within the casting form, and thereafter positioning the casting form with polymerized material therein over at least two teeth within the corresponding dental arch of the patient.

The mandibular advancement system associated with the second aspect may also be assembled directly on the teeth of the patient. That is, the casting form with the polymerizable material therein may be disposed over at least two teeth on one side of a particular dental arch of the patient so as to position the casting form mandibular advancement incline in the above-noted position. The polymerizable material may then be totally cured to a desired degree of rigidity within the mouth of the patient. This may entail directing an appropriate light source at the casting form to cure the polymerizable material therewithin. Enhancement of this type of curing operation is realized by forming the casting form from a material with at least a certain degree of transparency.

As noted, the various features discussed above in relation to the first aspect of the present invention may be incorporated in this second aspect as well. For instance, the casting form with the polymerizable/polymerized material therein may be installed by itself on one side of one of the patient's dental arches for providing a mandibular advancement incline for affecting mandibular advancement. Any of the crowns or the band discussed above in relation to the first aspect of the present invention may also be disposed within the casting form and thereby integrated therewith for providing a mandibular advancer in association with this second aspect and which is attached to the corresponding side of the corresponding dental arch of the patient.

A third aspect of the present invention relates to a crown for affecting mandibular advancement. This particular crown includes a crown occlusal surface which is disposable over an occlusal surface of a tooth within a given dental arch. An annular crown skirt extends away from this crown occlusal surface, toward the patient's gingiva when installed on a tooth, and about this tooth at this time as well. The crown of this third aspect further includes a crown mandibular advancement incline for affecting mandibular movement. In this regard, the crown mandibular advancement incline may be a substantially planar surface or may be defined by a line which is rotated about a reference axis which is disposed at least generally parallel with a tooth-long axis of the tooth on which the corresponding crown is installed (e.g., having a curvature disposed about such an axis), is disposed at an angle relative to the occlusal plane associated with the corresponding dental arch when the crown in installed, and further extends at least substantially perpendicularly across the major axis of the corresponding dental arch when the crown is installed (e.g., the crown mandibular advancement incline extends at least generally from a lingual surface of the crown to a buccal surface of the crown).

Various refinements exist of the features noted in relation to the subject third aspect of the present invention. Further features may also be incorporated in the subject third aspect of the present invention as well. These refinements and additional features may exist individually or in any combination. The crown mandibular advancement incline may be incorporated in the crown occlusal surface. For instance, the crown occlusal surface may include first and second sections which are disposed at different elevations on the crown occlusal surface, and the crown mandibular advancement incline may extend between these first and second sections (e.g., at a more "interior" portion of the crown occlusal surface). Another way of characterizing this configuration is that the crown occlusal surface includes a discrete raised section, with the crown mandibular advancement incline being that surface which defines a sidewall which interconnects this raised section with a remainder of the crown occlusal surface.

The crown mandibular advancement incline of the subject third aspect may also define at least substantially the entirety of the crown occlusal surface of its corresponding crown. This embodiment is particularly suited for installation on each of the patient's first molars (both upper first molars and both lower first molars). In this embodiment, the crown mandibular advancement incline may be oriented so as to be disposed at an angle of no more than about 20° relative to a plane which is parallel with the occlusal plane of the dental arch on which this crown is installed.

The crown mandibular advancement incline associated with the subject third aspect may also be disposed on either the mesial or distal end of the crown. In one embodiment of this configuration, the crown mandibular advancement incline is more specifically disposed at least generally where the crown occlusal surface and skirt would otherwise normally intersect. The crown mandibular advancement incline also may be disposed on an extension which projects away from the annular crown skirt. The crown mandibular advancement incline in this case is thereby disposed beyond the "oval" of the crown on the "free" end of this extension (e.g., at the end of this cantilever). Stated another way, the crown mandibular advancement incline in this case is disposed on an end of the extension which is opposite that which interfaces with the crown skirt. This particular embodiment may be effective at the more advanced stages of the treatment of a Class II or III malocclusion by moving the activating surface (e.g., the crown mandibular advancement incline) more mesially or distally to account for that amount of mesial or distal movement of the mandible which has already been achieved, as the case may be.

In each of the above described instances of a crown in accordance with the subject third aspect of the present invention, there may be a relatively significant gap between the entirety of the crown occlusal surface and the occlusal surface of the tooth on which the crown is disposed within the subject dental arch. Conventional crowns contact at least portions of the occlusal surface of the corresponding tooth. The "headroom" which may be incorporated into the crown of the subject third aspect may account for a desired positioning of the crown mandibular advancement incline. In one embodiment, there is at least about a 1.5 mm minimum gap between the crown occlusal surface at its apex and the occlusal-most surface of the tooth over which this crown is disposed when installed within the mouth of the patient. This space may be filled with an appropriate polymerizable material or may be left as an empty space when the crown is installed on the patient.

Those portions of the crown occlusal surface which do not define the crown mandibular advancement incline may assume a variety of shapes or configurations in relation to the crown of the subject third aspect. For instance, these portions of the crown occlusal surface may be substantially flat or planar, preferably such that the same are disposed at least generally in parallel relation with the occlusal of the dental arch on which the crown is installed. These portions of the crown occlusal surface may also be anatomically-shaped so as to at least generally approximate the underlying profile of the occlusal surface of the tooth on which the crown is installed.

A fourth aspect of the present invention is a crown which includes a crown occlusal surface which is disposable over an occlusal surface of a tooth within a dental arch of a patient. An annular crown skirt extends away from this crown occlusal surface, toward the patient's gingiva when installed on a tooth, and about this tooth as well. In this fourth aspect of the present invention, the crown occlusal surface is planar.

Various refinements exist of the features noted in relation to the subject fourth aspect of the present invention. Further features may also be incorporated in the subject fourth aspect of the present invention as well. These refinements and additional features may exist individually or in any combination. A crown mandibular advancement incline frame may be separately attached to the crown occlusal surface of the crown of the subject fourth aspect (e.g., spot welded, brazed). Stated another way, the crown mandibular advancement incline frame and crown in this case are separate parts, and are thereby not formed from a single piece of material (i.e., there is at least one joint therebetween). This particular crown mandibular advancement incline frame includes first and second frame sections which are configured such that there is an acute angle therebetween. The first crown frame section is disposed on and is appropriately attached to the crown occlusal surface (e.g., via one or more spot welds, via brazing) so that the second frame section extends away from both the first frame section and the crown occlusal surface. The second frame section may therefore be characterized as a crown mandibular advancement incline, and such may be a flat, planar surface. In one embodiment, the first frame section extends beyond the crown occlusal surface such that the second frame section is disposed at an interproximal location between two teeth within the dental arch on which the crown is installed. In any case, the first frame section is mounted on the crown occlusal surface such that the second frame section at least generally extends away form the crown occlusal surface.

Enhancement of the interconnection between the crown and the crown mandibular advancement incline frame may be realized by incorporating at least one, and more preferably a plurality of, apertures which extend through the entire occlusal-gingival extent of the first frame section. At least one of these apertures may be disposed so as to expose a portion of the crown occlusal surface on which the first frame section overlies. Polymerized material may occupy the entire extent of any such apertures. At least one aperture may also be disposed on that portion of the first frame section which extends beyond the crown occlusal surface. This may facilitate the directing of polymerizable material within the space defined between the first and second frame sections. Polymerizable material may be captured within this space between the first and second frame sections by having a pair of extensions which project from the opposite sides of the first frame section at least toward the "free" end of the second frame section or an apex of the second frame section.

A fifth aspect of the invention is embodied in a crown which includes a crown occlusal surface and an annular crown skirt which extends gingivally therefrom when the crown is installed on a tooth in a given dental arch. At least substantially an entirety of, and more preferably the entirety of, the crown occlusal surface is defined by a crown mandibular advancement incline. Preferably this crown mandibular advancement incline is an at least substantially flat, planar surface. In one embodiment, this crown mandibular advancement incline is oriented so as to be disposed at an angle of no more than about 20° relative to a reference plane which is parallel with the occlusal plane of the dental arch on which the crown is installed. This makes the crown of the subject fifth aspect particularly suited for installation on a patient's first molars. Crowns in accordance with the subject fifth aspect may be installed on both upper first molars and both lower first molars for affecting mandibular advancement. The crown mandibular advancement inclines installed on the upper first molars will engage with their corresponding crown mandibular advancement incline installed on the opposing lower first molar to affect mandibular advancement.

Various combinations of the casting forms and crowns/bands may be utilized to install a mandibular advancement incline on the same side of the upper and lower arches of the patient to cooperate for affecting mandibular advancement. For instance, the casting form with polymerized material therein may be fixed to one side of the patient's upper dental arch, and any of the above-noted crowns/band having a mandibular advancement incline associated therewith may be installed on the patient's lower dental arch to cooperate therewith to affect mandibular advancement, or vice versa. In addition, a casting form with one of the above-noted crowns or band and polymerized material therein may be fixed to one side of the patient's upper dental arch, and any of the above-noted crowns or band having a mandibular advancement incline associated therewith may be installed on the patient's lower dental arch to cooperate therewith to affect mandibular advancement, or vice versa. Moreover, a casting form with polymerized material therein may be fixed to one side of the patient's upper dental arch, and another casting form with polymerized material therein may be fixed to one side of the patient's lower dental arch to cooperate therewith to affect mandibular advancement. Finally, any of the above-noted crowns or band having a mandibular advancement incline associated therewith may be installed on the patient's upper dental arch, and any of the above-noted crowns or band having a mandibular advancement incline associated therewith may be installed on the patient's lower dental arch to cooperate therewith to affect mandibular advancement.

A sixth aspect of the present invention is generally directed toward providing enhanced occlusal support during movement of a patient's mandible. In this regard, an appropriate mandibular advancer will typically be installed on both sides of the patient's upper and lower dental arches. This may and likely will cause the patient to be unable to seat the upper dental arch entirely on the lower dental arch (i.e., engagement of opposing mandibular advancers will keep the upper and lower dental arches in spaced relation). One way to address this condition is to install at least one crown having an enhanced occlusal-gingival extent (in relation to conventional crowns and how the same typically are disposed relative to the gingiva) on each side of the patient's upper and/or lower dental arch, typically at a location which is mesial of the mandibular advancer(s) that is installed on the same side of the same dental arch. In any case, a space exists between the occlusal surface of the tooth on which the crown is installed and the interior of the occlusal surface of the crown (e.g., in the manner contemplated by the seventh aspect discussed below). The occlusal surface of this "taller" crown will at least at some point in time during treatment engage a tooth disposed on the opposing dental arch to provide occlusal support at a location other than that where mandibular treatment forces are being generated (e.g., other than where opposing mandibular advancers are engaged).

A seventh aspect of the present invention is generally directed to a crown which may be used in at least some aspect of mandibular movement treatment/therapy. This particular crown has an enhanced occlusaal-gingival extent in that its crown occlusal surface is disposed in spaced relation to the occlusal surface of the underlying tooth on which the crown is installed, even though its gingival extreme is disposed at or below/under the patient's gingiva. In one embodiment, the minimum vertical extent of this space is at least about 1.5 mm as measured along the tooth-long axis. That is, there is at least about a 1.5 mm space between each point on the occlusal surface of the tooth and that point on the interior of the occlusal surface of the crown which is disposed therebeyond along a reference axis which is parallel with the tooth-long axis.

Various refinements exist of the features noted in relation to the subject seventh aspect of the present invention. Further features may also be incorporated in the subject seventh aspect of the present invention as well. These refinements and additional features may exist individually or in any combination. For instance, the crown of the subject seventh aspect may include an mandibular advancement incline of any of the types noted above in relation to the third and fifth aspects noted above. Another surface for providing an active force for mandibular advancement may be the transition section between the crown occlusal surface and the crown skirt (e.g., a generally convexly arcuate surface on both the mesial and distal of the crown). Alternatively, the crown of the subject sixth aspect may be used for providing enhanced occlusal support in the manner addressed by the above-noted sixth aspect.

An eighth aspect of the present invention is directed to a cap and band which are interconnected in a certain manner to define a mandibular advancer. The cap includes a cap occlusal surface, a cap skirt, and at least one "active" surface for affecting mandibular advancement (e.g., a mandibular advancement incline). The occlusal-gingival extent of the cap is less than that of the occlusal-gingival extent of the exposed enamel of the tooth on which the cap is mounted (e.g., the gingival edge of the cap is disposed in spaced relation to the patient's gingiva). One wire extends from each of the buccal and lingual sides of the cap for attachment to the band. In this regard, the band includes appropriate structure on each of its buccal and lingual sides for interfacing with these wires to orient the cap on the tooth and interconnect the cap with the band.

Various refinements exist of the features noted in relation to the subject eighth aspect of the present invention. Further features may also be incorporated in the subject eighth aspect of the present invention as well. These refinements and additional features may exist individually or in any combination. The cap occlusal surface may be disposed in spaced relation to the occlusal surface of the tooth on which the cap is mounted. Those spacings discussed above in relation to the seventh aspect may be utilized by the subject eighth aspect as well. With regard to the "active" surface of the cap, any of the mandibular advancement inclines discussed above in the third and fifth aspects for crowns may be incorporated into the cap associated with the subject eighth aspect. Another surface for providing an active force for mandibular advancement may be the transition section between the cap occlusal surface and the cap skirt (e.g., a generally convexly arcuate surface on both the mesial and distal of the cap). The components of the subject eighth aspect could also be used to provide the functionality of the sixth aspect discussed above.

Both of the wires may include a first section which is at least generally occlusally-gingivally disposed, and a second section which is at least generally mesially-distally disposed. One of these wires may interface with a buccal tube disposed on and attached to the buccal side of the band. The other of these wires may be disposed under a catch disposed on and attached to the lingual side of the band. A ligating tube may also be disposed on and attached to the lingual side of the band for using a ligature wire to further secure the wire which interfaces with the catch.

BRIEF DESCRIPTION OF THE SEVERAL VIEWS OF THE DRAWING

FIG. 19 is a perspective view of another embodiment of a crown mandibular advancer.

FIG. 20A is a side view, looking toward the lingual, of the crown mandibular advancer of FIG. 19 when installed on both the upper and lower dental arches of a patient.

FIG. 20B is an end view, looking from the distal and towards the mesial, of the arrangement illustrated in FIG. 20A.

DETAILED DESCRIPTION OF THE INVENTION

Figure 1A:
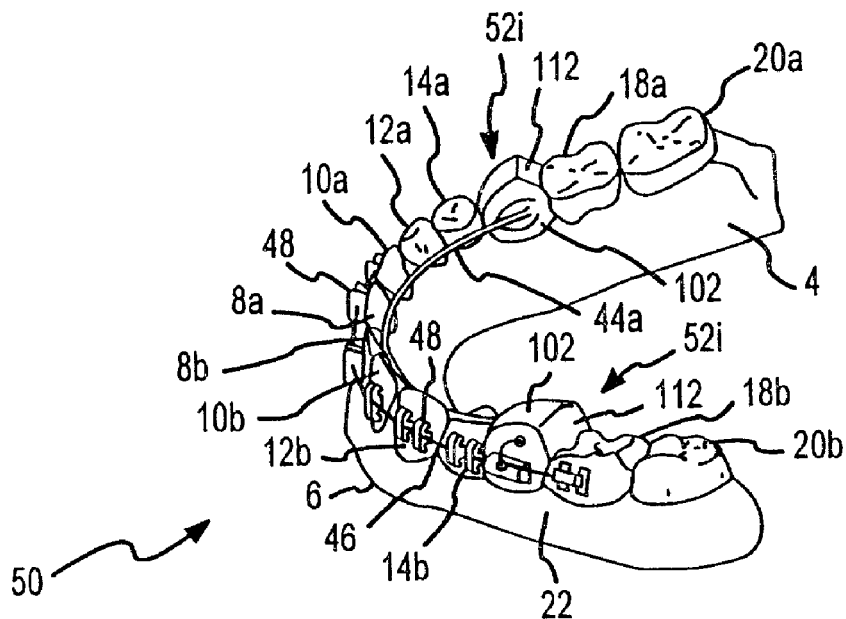
FIG. 1A is a perspective view of a lower dental arch of a patient with one embodiment of a pair of crown mandibular advancers disposed on opposite sides of the lower dental arch.
Figure 1B:
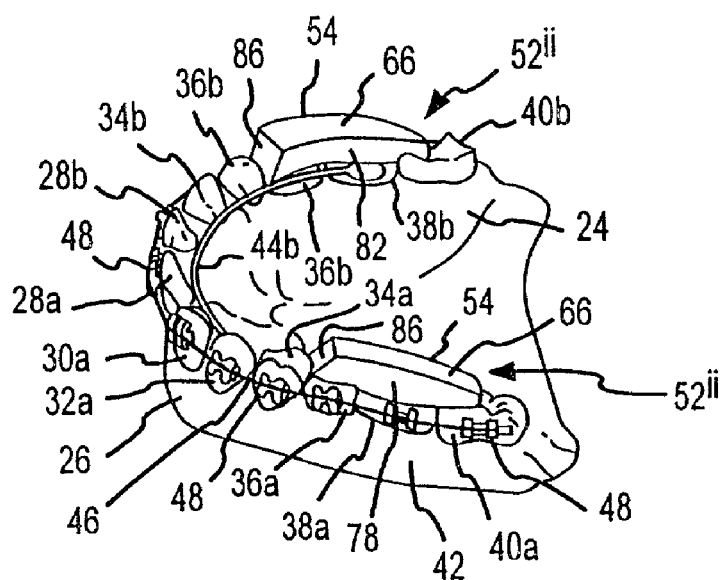
FIG. 1B is a perspective view of an upper dental arch of a patient with one embodiment of a pair of casting form mandibular advancers disposed on opposite sides of the upper dental arch.

The present invention will now be described in relation to the accompanying drawings which at least assist in illustrating its various pertinent features. FIGS. 1A–B illustrate a mandible 4 and maxilla 24 of a patient. The mandible 4 includes a lower dental arch 6 having two sides—one side using an "a" designation for its corresponding teeth and with the opposite side using a "b" designation for its corresponding teeth. Each side of the lower dental arch 6 includes the following teeth which extend from a lower gingiva 22 of the patient: a lower central 8, a lower lateral 10, a lower cuspid 12, a lower first bicuspid 14, a lower second bicuspid 16, a lower first molar 18, and a lower second molar 20. The maxilla 24 includes an upper dental arch 26 having two sides—one side using an "a" designation for its corresponding teeth and with the opposite side using a "b" designation for its corresponding teeth. Each side of the upper dental arch 26 includes the following teeth which extend from an upper gingiva 42 of the patient: an upper central 28, an upper lateral 30, an upper cuspid 32, an upper first bicuspid 34, an upper second bicuspid 36, an upper first molar 38, and an upper second molar 40. Teeth on the "a" side of the lower arch dental arch 6 interface with teeth on the "a" side of the upper dental arch 26, while teeth on the "b" side of the lower dental arch 6 interface with teeth on the "b" side of the lower dental arch 26. Both the lower dental arch 6 and the upper dental arch 26 have an orthodontic arch 44.installed on the lingual side thereof (and therefore a lingual arch 44), and orthodontic brackets 48 installed on the buccal side thereof with an arch wire 46 passing through the various brackets 48.

A mandibular advancement system 50 is disclosed herein which utilizes a pair of mandibular advancers 52 which are installed on opposite sides of the lower dental arch 6. The system 50 further utilizes another pair of mandibular advancers 52 which are installed on opposite sides of the upper dental arch 26. Those mandibular advancers 52 which are installed on opposite sides of the upper dental arch 26 interface with an mandibular advancer 52 which is on the same side, but on the lower dental arch 6, to affect mesial or distal advancement of the mandible 4, depending upon the positioning of the "active" surfaces of these advancers 52. Preferably, each such "active" surface is flat or planar with an area of at least about 13 mm², is disposed at an angle relative to an occlusal plane of a dental arch on which the subject mandibular advancer 52 is disposed, and further is disposed to extend at least substantially across or perpendicular to the major axis of such dental arch. Various configurations for the mandibular advancers 52 are presented herein. Each of these various mandibular advancers 52 may be utilized in an mandibular advancement system 50. Although the accepted nomenclature of the adult teeth have been presented herein and will be used in the description of the mandibular advancers 52, it should be appreciated that these mandibular advancers 52 are applicable to children. Different nomenclature is commonly used to describe a child's teeth. Nonetheless, the advancers 52 will be installed on the tooth or teeth of a child which positionally correspond to those adult teeth identified herein.

Figure 2:
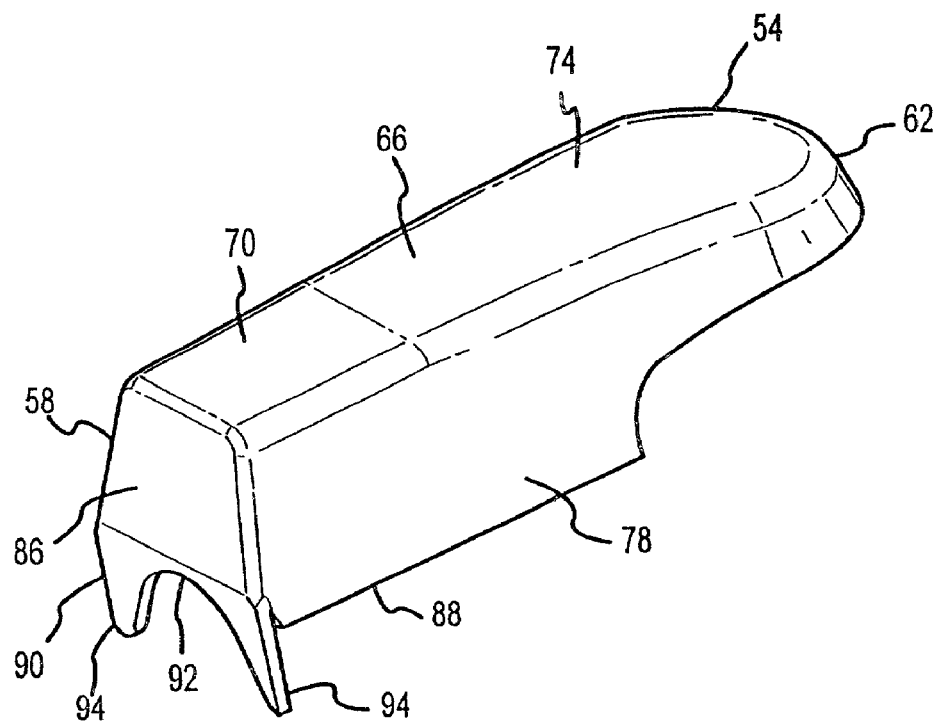
FIG. 2 is a perspective view of a casting form used by the embodiment of the casting form mandibular advancer presented in FIG. 1B.
Figure 3:
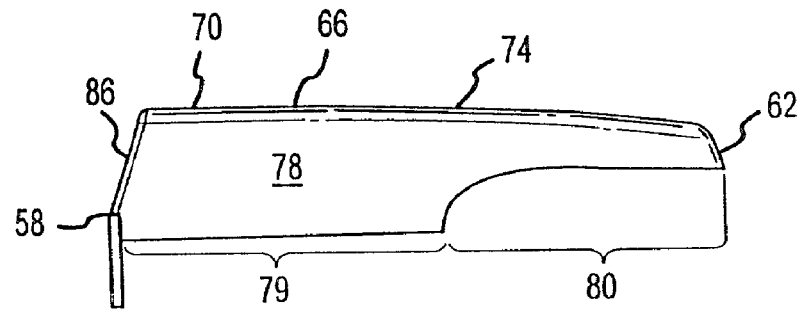
FIG. 3 is a side view of the casting form of FIG. 2.
Figure 4:
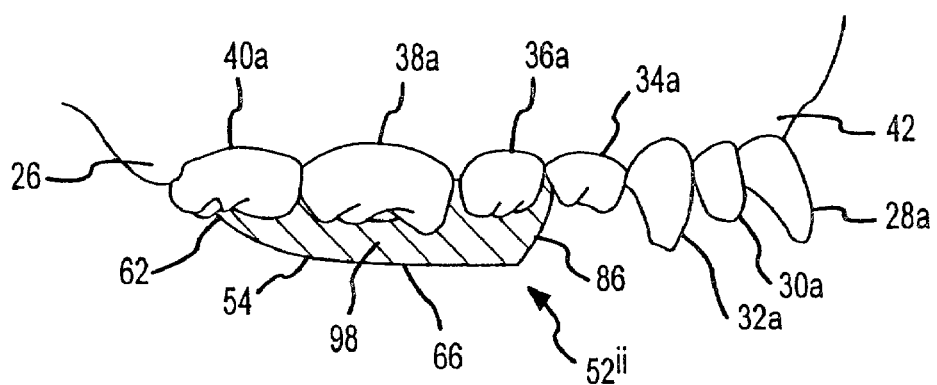
FIG. 4 is a cutaway side view of one side of an upper dental arch of a patient with the embodiment of the casting form mandibular advancer presented in FIG. 1B being shown in cross-section thereon.

Details of one embodiment of a mandibular advancer 52 are presented in FIGS. 1B and 4, with certain components thereof being illustrated in FIGS. 2–3. The mandibular advancer 52$^{ii}$ of FIGS. 1B and 4 includes a casting form 54 which functions as a "bathtub" of sorts and which is also illustrated in FIGS. 2–3. Generally a "flowable" material is disposed within the casting form 54 such that this material may be "molded" to conform to at least two teeth of a patient, and thereafter "cured" (e.g., polymerized) into an at least substantially rigid form such that the mandibular advancer 52$^{ii}$ is available for the application of mandibular advancement forces to the patient. In this regard, a casting form occlusal surface 66, a casting form buccal skirt 78, a casting form lingual skirt 82, and a casting form mandibular advancement incline 86 collectively define a hollow repository or containment space 88 in which this "flowable" material may be disposed through the "open" side of the casting form which is disposed opposite the casting form occlusal surface 66.

The casting form mandibular advancement incline 86 is disposed on a first end of the casting form 54. This incline 86 is an at least substantially flat, planar surface and is/defines the "active" surface of an mandibular advancer 52 which incorporates such a casting form 54. That is, the incline 86, or an underlying material/structure disposed in at least substantially parallel and interfacing relation therewith, engages the "active" surface of a mandibular advancer 52 disposed on the same side of the opposing dental arch to affect mandibular advancement. In one embodiment, the size of the incline 86 has a length which is within a range of about 5 mm to about 7 mm and a width which is within a range of about 3 mm to about 5 mm. FIG. 1B illustrates that mesial advancement of the mandible 4 may be affected by having the mandibular advancer 52$^{ii}$ installed on the upper dental arch 26 and by having the casting form mandibular advancement incline 86 project at least generally mesially. Distally directed advancement of the mandible 4, or a retraction of the mandible 4, could be affected by having the mandibular advancer 52$^{ii}$ installed on the upper dental arch 26 and by having the casting form mandibular advancement incline 86 project at least generally distally. Similarly, the mandibular advancer 52$^{ii}$ could be installed on the lower dental arch 6 to affect mesial advancement of the mandible 4 (by having the casting form mandibular advancement incline 86 project at least generally distally) or to affect distal advancement of the mandible 4 (by having the casting form mandibular advancement incline 86 project at least generally mesially).

The casting form mandibular advancement incline 86 is disposed at least substantially across or perpendicular to the major axis of the dental arch on which it is disposed (i.e., extending from the buccal to the lingual). Moreover, the incline 86 is disposed at an angle of about 20 degrees relative to vertical in the embodiment of the mandibular advancer 52$^{ii}$ presented in FIGS. 1B and 4. Other angular dispositionings of the casting form mandibular advancement incline 86 may be utilized to affect mandibular movement by the desired camming-like action (e.g., 45 degrees). However, the noted 20 degree angle is believed to reduce the potential for the casting form mandibular advancement incline 86 becoming inadvertently disengaged with the "active" surface of its opposing mandibular advancer 52 (the crown mandibular advancement incline 112 in the case where the mandibular advancer 52$^{ii}$ is used in combination with the mandibular advancer 52$^{i}$, as presented in FIGS. 1A–B) during treatment to affect mandibular advancement. When installed on a given dental arch, this then disposes the casting form mandibular advancement incline 86 at an angle to the occlusal plane of the subject dental arch. In the noted embodiment the casting form mandibular advancement incline 86 will be disposed at an angle of about 70 degrees relative to this particular occlusal plane. Unless otherwise noted herein, the "active" surface of each of the mandibular advancers 52 addressed herein will be oriented similarly to the casting form mandibular advancement incline 86 when mounted on the subject dental arch.

The casting form 54 shown in FIGS. 1B and 2–4 includes a second end 62 which is disposed opposite the first end 58 having the casting form mandibular advancement incline 86. These ends 58 and 62 are separated by a distance such that the casting form 54 will overlie at least two entire teeth of a patient, and possibly at least part of a third tooth, when the advancer 52$^{ii}$ is installed on the subject dental arch. The second end 62 curves from the casting form buccal skirt 78 to the casting form lingual skirt 82 of the casting form 54 for purposes of extending any mandibular advancer 52 which uses the casting form 54 to cover the occlusal surfaces of adjacent teeth in the subject dental arch, to assist in gaining adequate fixation, and to incorporate these teeth in an anchorage unit, as a means of resistance, in order to apply forces sufficient to advance the mandible 4. In one embodiment, this particular curvature is defined by a radius. Typically the second end 62 of the casting form 54 is disposed directly on one of the teeth of the dental arch of the patient on which the casting form 54 is installed. Stated another way, the casting form 54 is typically not installed such that its second end 62 "extends around" one of the teeth of the dental arch of the patient on which the casting form 54 is installed.

The casting form 54 may be disposed between a pair of adjacent teeth within the dental arch of a patient on which the casting form 54 is installed. In this regard, the casting form 54 may include an extension 90 which is disposed on its first end 58 and which extends further gingivally from the gingival extreme of the casting form mandibular advancement incline 86. This extension 90 is configured so as to "straddle" the dental arch on which the casting form 54 is installed. A generally u-shaped aperture 92 defined by a pair of spaced-apart prongs 94 provides this function. In the illustrated embodiment, the occlusal-gingival extent of the casting form 54 at its first end 58 with the extension 90 thereon is greater than the occlusal-gingival extent of adjacent portions of both the casting form buccal skirt 78 and the casting form lingual skirt 82. This need not always be the case. For instance, the first end 58 of the casting form 54 may have the same occlusal-gingival as that of the adjacent portion of the casting form buccal skirt 78 and/or the casting form lingual skirt 82.

The casting form buccal skirt 78 and the casting form lingual skirt 82 are disposed in spaced relation. In one embodiment the casting form buccal skirt 78 and the casting form lingual skirt 82 are sufficiently spaced such that the casting form 54 may extend along at least a portion of the lingual and/or buccal sides of the dental arch on which the casting form 54 is installed. Material within the casting form 54 may then be disposed between the casting form 54 and at least part of these lingual and/or buccal surfaces of the dental arch. This may serve to increase the "robustness" of the installation of the casting form 54 on the subject dental arch. It may also be desirable for the casting form 54 to cover or partially/totally encapsulate or encase orthodontic armamentarium installed on these lingual and/or buccal surfaces of the subject dental arch. Further increases of the "robustness" of the interconnection of the casting form 54 with the subject dental arch may be realized by having the casting form 54 cover or encapsulate a corresponding lingual arch 44.

The entire longitudinal extent of the casting form 54 need not extend along the lingual and/or buccal sides of the corresponding dental arch to the same occlusal-gingival extent. One or both of the casting form buccal skirt 78 and the casting form lingual skirt 82 may have a different occlusal-gingival extent at one or more places between the first end 58 of the casting form 54 and the second end 62 of the casting form 54. In the illustrated embodiment, a first buccal skirt section 79 which extends from the first end 58 has a larger occlusal-gingival extent than a second buccal skirt section 80 which extends from an end of this first section 79 to the second end 62 of the casting form 54. The casting form lingual skirt 82 may be similarly configured. This "two-tiered" occlusal-gingival extent provides the benefit of greater flexibility with the facility to fit the casting form 54 over several teeth with the depth of the casting form buccal skirt 78 and/or casting form lingual skirt 82 to be varied according to the contours of the corresponding teeth, and of any lingual or buccal attachments (e.g., brackets, wires, or tubes) which may be fitted as part of an orthodontic appliance.

Other contours may be employed on one or both of the casting form buccal skirt 78 and the casting form lingual skirt 82 of the casting form 54. Significant flexibility is provided as to the actual configuration of both the casting form buccal skirt 78 and the casting form lingual skirt 82 by making the casting form 54 from materials (e.g., thermoform plastics) which allow orthodontic laboratory personnel or orthodontic practitioners to customize the casting form 54 to the needs of the particular treatment application and/or patient by cutting the casting form 54 into the desired profile. For instance, one or more enclosed apertures (i.e., holes) or open apertures (i.e., those which interface with the gingival edge of the casting form 54) may be cut in one or both of the casting form buccal skirt 78 and the casting form lingual skirt 82 so as to keep the casting form 54 from covering certain orthodontic armamentarium when the casting form 54 is installed on the subject dental arch of the patient (not shown).

Engagement of the casting form mandibular advancement incline 86 by the "active" surface of the mandibular advancer 52 disposed on the opposing dental arch is used to affect mesial or distal advancement of the mandible 4 by what may be characterized as a "camming-like" action as noted. Typically the patient will have to move the mandible 4 in order to establish this engagement. In this regard, the casting form occlusal surface 66 of the casting form 54 is contoured to facilitate this engagement. The casting form occlusal surface 66 includes a first section 70 and a second section 74 that are disposed in different orientations. The first section 70 of the casting form occlusal surface 66 is at least substantially flat or planar, and is intended to be disposed at least generally parallel with the occlusal plane of the dental arch when the casting form 54 is installed thereon. The opposing mandibular advancer 52 may "slide" on this first section 70 to engage the "active" surfaces of the corresponding mandibular advancers 52. The second section 74 of the casting form occlusal surface 66 is also at least substantially flat or planar. However, the end of the second section 74 corresponding with the second end 62 of the casting form is more gingivally disposed than the end of the second section 74 which is adjacent to the first section 70. That is, the second section 74 slants gingivally progressing from the first section 70 toward the second end 62 of the casting form 54. Configuring the second section 74 in this manner provides the benefit of a wedge-shaped occlusal casting form 54, which is thicker at the first section 70 than at the second section 74, and thinner at the second end 62. This is to accommodate the natural contours of the opposing teeth when the jaws are closed. Consider the case when the casting form 54 is installed on the upper dental arch 26. When the teeth are slightly apart with the mandible 4 and maxilla 24 slightly open, the space between the lower first molar 18 and upper first molar 38 and the space between the lower second molar 20 and the upper second molar 40, is slightly less than the space between the lower first bicuspid 14 and the upper first bicuspid 34 (in a child, these teeth are more commonly referred to as the lower and upper first deciduous molars, respectively, or the "D") and the space between the lower second bicuspid 16 and the upper second bicuspid 36 (in a child, these teeth are more commonly referred to as the lower and upper second deciduous molars, respectively, or the "E"). The wedge-shaped profile of the casting form 54, when installed on the upper dental arch 26, is designed to accommodate this feature as it is thinner (occlusally-gingivally) posteriorly and thicker (occlusally-gingivally) anteriorly.

As noted above, the casting form 54 is formed from a material which may be cut by orthodontic laboratory personnel or orthodontic practitioners to customize the configuration of the casting form 54 to the dental arch of the patient on which the casting form 54 will be installed. Moreover, preferably the material from which the casting form 54 is made will also "cross-link" with the flowable material disposed therein when the same is cured. That is, the flowable material which is disposed within the repository 88 of the casting form 54 is cured to a desired degree of rigidity to define a polymerized material 98 within the casting form 54, and which is illustrated in FIG. 4 and which will be discussed in more detail below. This "curing" of the flowable material into the polymerized material 98 preferably chemically interconnects the polymerized material 98 with the casting form 54, although it may be possible to not have a cross-linking between the casting form 54 and the polymerized material 98 therewithin. In one embodiment, the casting form 54 is made from thermoform plastics and the flowable material is a traditional/customary composite resin.

Installation of the mandibular advancer 52[a] utilizing the casting form 54 discussed above may be affected in a number of different manners on the subject dental arch. Consider the example presented in FIG. 1B where the mandibular advancer $52^{ii}$ is installed on the upper dental arch 26. One way to install the mandibular advancer $52^{ii}$ involves the use of a stone casting. In this case a stone casting is made of the upper dental arch 26 of the patient at issue. This will typically be done "chair side" by an orthodontic practitioner. The orthodontic practitioner will then typically send the stone casting to an orthodontic laboratory for production of a customized mandibular advancer $52^{ii}$ for each of the two sides of the upper dental arch 26. One or more orthodontic appliances may need to be attached to the lingual and/or buccal sides of the dental arch 26 to affect the desired orthodontic treatment. Portions of the casting form buccal skirt 78 and/or the casting form lingual skirt 82 of the casting form 54 may be trimmed to accommodate exposure of one or more of these orthodontic appliances when the mandibular advancer $52^{ii}$ is installed on the upper dental arch 26. In any case, an appropriate release agent is first applied to the occlusal, lingual, and buccal surfaces of the stone casting of the upper dental arch 26 in the region where the casting form 54 is to be installed. An appropriate flowable material is disposed within the casting form 54 and the same is then disposed over the stone casting of the upper dental arch 26. The extension 90 straddles the stone casting of the upper dental arch 26 such that the opposing prongs 94 are disposed on the buccal and lingual sides of the stone casting between the stone casting of the upper second bicuspid 36 and the upper first bicuspid 34. Both the stone casting of the upper second bicuspid 36 and the stone casting of the upper first molar 38 are totally covered by the casting form 54 with the flowable material therein. Only a portion of the stone casting of the upper second molar 40 is covered by the casting form 54 in that the second end 62 of the casting form 54 engages an occlusal surface of the stone casting of the upper second molar 40. However, the casting form 54 could be configured to cover the entirety of the second molar 40 as well (not shown).

Once on the stone casting of the upper dental arch 26, the casting form 54 is seated thereon into the desired position. Preferably this involves disposing the first section 70 of the casting form occlusal surface 66 in at least generally, and more preferably in at least substantially parallel relation with the occlusal plane of the stone casting of the upper dental arch 26. This is usually only visually determined by the orthodontic laboratory technician. At least part of the casting form mandibular advancement incline 86 will be occlusally-gingivally aligned with at least a mesial portion of the upper second bicuspid 36. However, with the casting form mandibular advancement incline 86 typically being disposed at an angle of about 20 degrees relative to vertical, at least about 7 mm of the mesio-distal extent of the upper second bicuspid 36 will typically underlie the first section 70 of the casting form 54. At least a mesial portion of the upper first molar 38 may underlie the first section 70 of the casting form occlusal surface 66 of the casting form 54 as well.

At least a partial curing of the flowable material within the casting form 54 occurs while the casting form 54 is installed on the stone casting of the upper dental arch 26. Curing may be affected simply by the passage of time and with the casting form 54 and the stone casting of the upper dental arch 26 being exposed to ambient conditions. Other techniques for at least partially curing the flowable material while the casting form 54 is mounted on the stone casting of the upper dental arch 26 may be utilized as well. One or more light sources may be directed at/through the casting form 54 to affect at least a partial curing of the flowable material which is retained between the casting form 54 and the stone casting of the upper dental arch 26. Once the flowable material has cured to the degree where it will at least substantially retain its shape within the casting form 54, the casting form 54 and the at least partially cured flowable material therein may be collectively removed from the stone casting of the upper dental arch 26 due to the use of the above-noted release agent. Completion of the curing of the flowable material may then be completed, such as by disposing the casting form 54 and the at least partially cured flowable material within an appropriate oven. Exactly how the flowable material is cured is not essential to the manufacture/use of a mandibular advancer 52 which utilizes a casting form 54.

Curing of the flowable material to the desired degree provides a polymerized material 98 within the casting form 54 (FIG. 4). The polymerized material 98 is sufficiently rigid so as to be able to withstand the forces which will be used to affect advancement of the mandible 4. That is, the polymerized material 98 is sufficiently rigid and strong to withstand the forces of occlusion of the teeth without distortion or breakage. The surface in contact with the teeth is accurately moulded to the teeth, so that a suitable dental adhesive can be used to fix the casting forms 54 to the teeth.

The mandibular advancer $52^{ii}$, which has been formed in the above-described manner, is now ready for installation on the patient. The orthodontic practitioner applies an appropriate orthodontic bonding system to least a portion of those surfaces of the mandibular advancer $52^{ii}$, and preferably the entirety thereof, which will interface with the upper dental arch 26 of the patient when installed thereon. The orthodontic practitioner then simply positions the mandibular advancer $52^{ii}$ on the upper dental arch 26 of the patient in the same position as the same was formed on the stone casting thereof in the above-noted manner. As can be seen in FIG. 4, the extension 90 of the casting form 54 is positioned between the upper first bicuspid 34 and the upper second bicuspid 36. The polymerized material 98 at least substantially conforms to the occlusal surface of the upper second bicuspid 36, the occlusal surface of the upper first molar 38, and part of the occlusal surface of the upper second molar 40. The polymerized material 98 also conforms to the spacing between the upper second bicuspid 36 and the casting form mandibular advancement incline 86, the spacing between the upper second bicuspid 36 and the upper first molar 38, and the spacing between the upper first molar 38 and the upper second molar 40. Furthermore, the polymerized material 98 extends along at least part of both the buccal and lingual surfaces of the entire mesio-distal extent of the upper second bicuspid 36 and the upper first molar 38, as well as part of the mesio-distal extent of the upper second molar 40. The "active" surface of the mandibular advancer $52^{ii}$ is the casting form mandibular advancement incline 86. However, the underlying polymerized material may also actually define the "active" surface of the mandibular advancer $52^{ii}$ should the material of the casting form mandibular advancement incline 86 "wear away" during treatment.

The mandibular advancer $52^{ii}$ can also be totally assembled and installed "chair side" by the orthodontic practitioner and at least generally in the above-noted manner. At least those teeth which will interface with the mandibular advancer $52^{ii}$ first must be sufficiently prepared (e.g., cleaned) so that a suitable bond can be established therewith by the advancer $52^{ii}$. The casting form 54 with a flowable material therein is disposed directly on the desired teeth of the upper dental arch 26. The flowable material in this instance also serves to establish a bond directly with the teeth that interface therewith. That is, the mandibular advancer $52^{ii}$ in this case is not removed from the upper dental arch 26 for curing. Instead, the flowable material is totally cured within the mouth of the patient to the desired degree by using an appropriate light source or the like. In this regard, it is desirable to form the casting form 54 from a material which is at least partially transparent.

Figure 5:
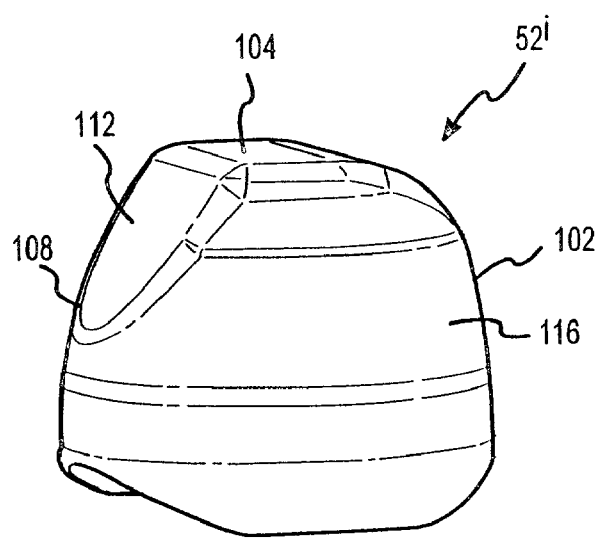
FIG. 5 is a perspective view of the embodiment of the crown mandibular advancer presented in FIG. 1A.
Figure 6:
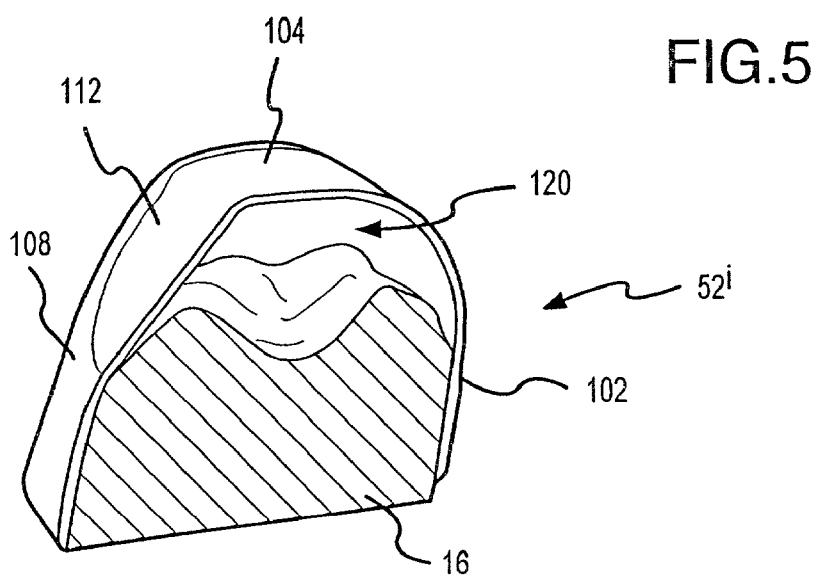
FIG. 6 is a perspective, cross-sectional view of the embodiment of the crown mandibular advancer presented in FIG. 5.
Figure 9:
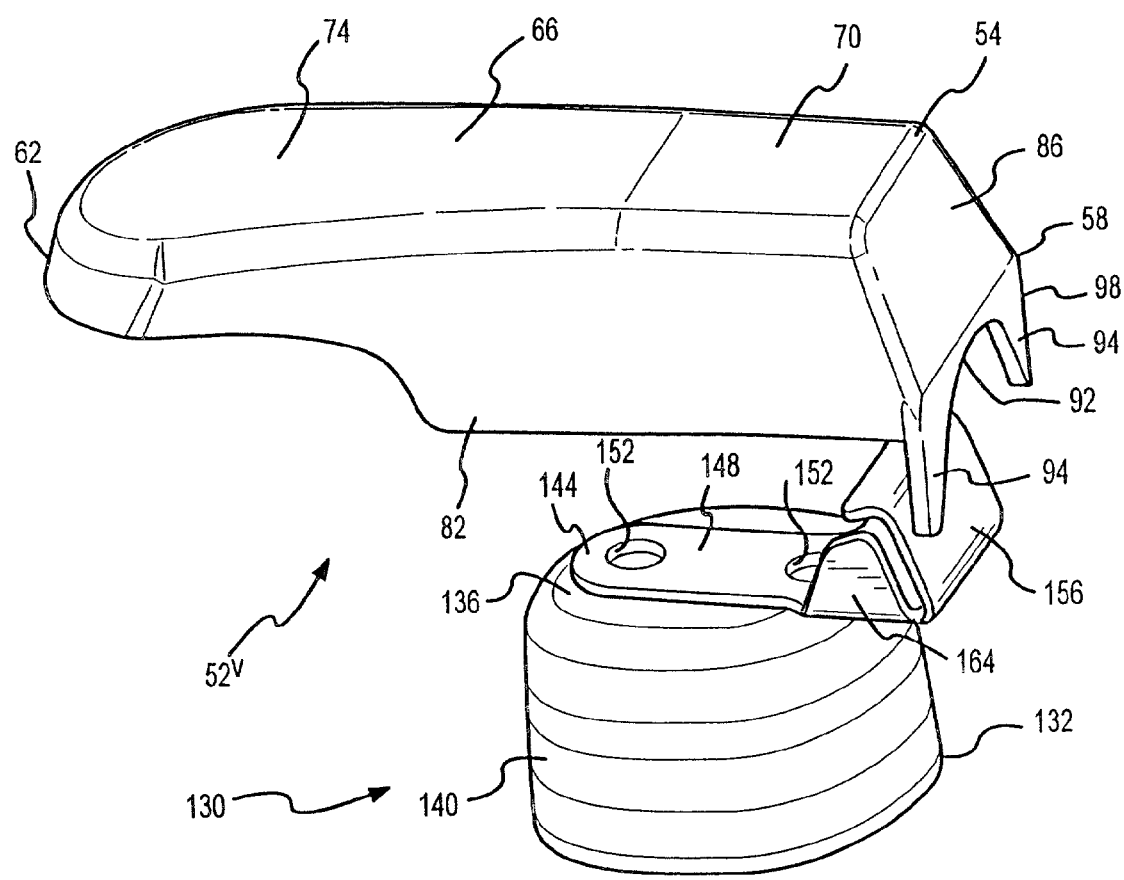
FIG. 9 is an exploded, perspective view of an embodiment of a combination casting form/crown mandibular advancer.
Figure 10:
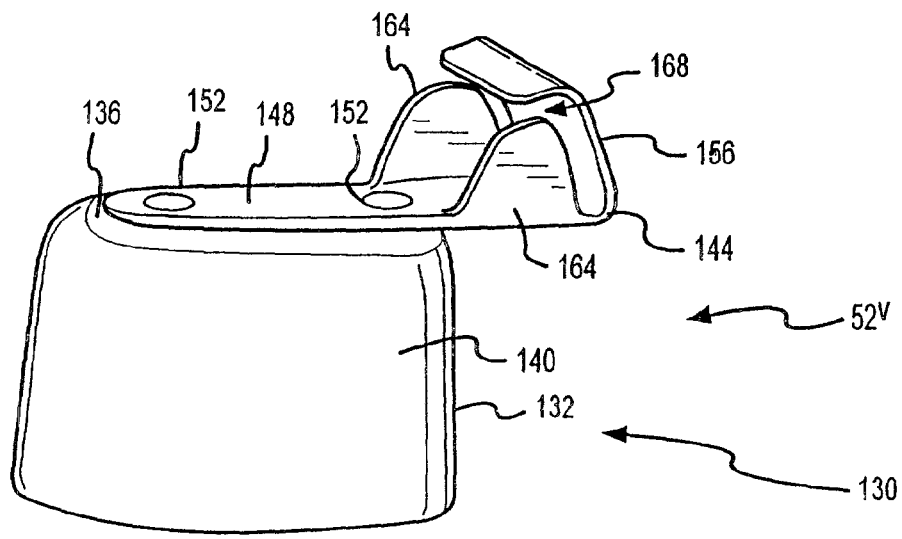
FIG. 10 is a perspective view of the crown assembly utilized by the embodiment of the combination casting form/crown mandibular advancer presented in FIG. 9.
Figure 11A:
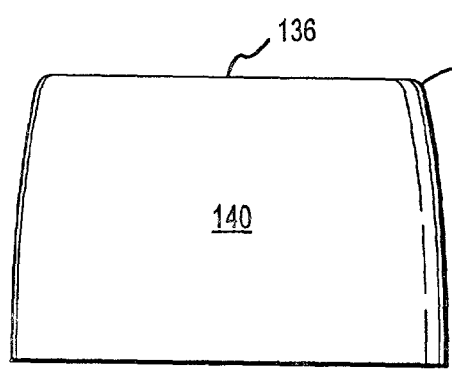
FIG. 11A is a side view of the crown from the crown assembly of FIG. 10.
Figure 11B:
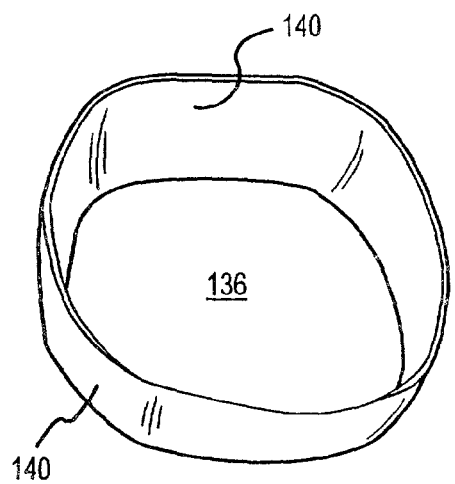
FIG. 11B is a perspective view of the interior of the crown from the crown assembly of FIG. 10.

Another embodiment of an mandibular advancer 52 which may be used by the mandibular advancement system 50 is presented in FIGS. 1A and 5–6. The mandibular advancer $52^i$ of FIGS. 1A and 5–6 includes a crown 102 which is installed over a tooth in the subject dental arch. In the mandibular advancement system 50 illustrated in FIG. 1A, the crown 102 of each mandibular advancer $52^i$ is installed on the lower second bicuspid 16 on each side of the lower dental arch 6. The crown 102 generally includes a crown occlusal surface 104 and an annular crown skirt 116 which extends away from the crown occlusal surface 104 and toward the corresponding gingiva when the crown is installed over a tooth within a given dental arch. A crown mandibular advancement incline 112 is disposed on an "end" 108 of the crown 102 which projects either mesially or distally when the crown 102 is installed over a tooth in the subject dental arch. The crown mandibular advancement incline 112 projects distally in the configuration presented in FIG. 1A. The "active" surface of the mandibular advancer $52^i$ is the crown mandibular advancement incline 112, and in one embodiment such is an at least substantially flat, planar surface.

The crown occlusal surface 104, the crown mandibular advancement incline 112, and the crown skirt 116 are integrally formed. Stated another way, the crown occlusal surface 104, the crown mandibular advancement incline 112, and crown skirt 116 are formed from a single piece of material such that there is no joint of any kind between any of these components. Materials which are commonly used to make conventional crowns may be used to make the crowns 102 here as well, such as stainless steel, titanium, gold, and aluminum. Other materials such as vacuum-formed plastics such as polycarbonate, acrylic, styrene, buturate, and vinyls may be used as well for the crowns 102. These materials would also be applicable for making the casting form 54 by vacuum-forming techniques.

As can be seen in FIG. 6, the crown 102 is "taller" than conventional crowns. When the crown 102 is installed over the desired tooth (a lower second bicuspid 16 in the case of the installation of the mandibular advancer $52^i$ presented in FIGS. 1A and 6), there is a space 120 between the occlusal surface of this tooth and the crown occlusal surface 104. In one embodiment, the minimum vertical extent of this space 120 is about 1.5 mm at its occlusal-most extreme or at the apex of the incline 112, and may be as much as about 4 mm at its occlusal-most extreme (both measured relative to an occlusal-most surface of the tooth 16 or the "peaks" of the subject tooth). A suitable orthodontic bonding system may be used to fixedly mount the crown 102 over/onto the subject tooth. These types of materials are sufficiently rigid when cured to enhance the support of the crown mandibular advancement incline 112. That is, an amount of orthodontic bonding system material may be positioned within the crown 102 before installing the same over the subject tooth such that the entirety of the space 120 is occupied by this orthodontic bonding system material when the crown 102 is installed over the subject tooth. Alternatively, the space 120 may remain as an "air gap" between the crown occlusal surface 104 and the occlusal surface of the tooth on which the crown 102 is mounted.

The existence of the space 120 facilitates the dispositioning of the crown mandibular advancement incline 112 in a desired position when installed over its corresponding tooth (e.g., disposed at an angle of about 70 degrees relative to a plane which is parallel with the occlusal plane associated with the dental arch having the tooth over which the crown 102 is installed). In this regard and as can be seen in FIG. 6, the gingival-most extreme of the crown mandibular advancement incline 112 initiates where the tip of the corresponding tooth begins to extend inwardly toward its tooth-long axis and is disposed in at least generally parallel relation therewith. The incline 112 continues to extend occlusally beyond the occlusal surface of the tooth 16. In one embodiment, the length of the crown mandibular advancement incline 112 is within a range of about 3 mm to about 5 mm, the width of the crown mandibular advancement incline 112 is within a range of about 5 mm to about 7 mm, and/or has an area within a range of about 13 mm$^2$ to about 15 mm$^2$.

Each of the two mandibular advancers $52^{ii}$ on the upper dental arch 26 cooperate with their own mandibular advancer $52^i$ on the lower dental arch 6 in order to affect mesial advancement of the mandible 4 in the particular configuration illustrated in FIGS. 1A–B. The casting form mandibular advancement incline 86 of the mandibular advancer $52^{ii}$ disposed on the "a" side of the upper dental arch 26, or the similarly contoured polymerized material 98 thereunder, cams relative to the crown mandibular advancement incline 112 of the mandibular advancer $52^i$ disposed on the "a" side of the lower dental arch 6 when disposed in interfacing relation therewith. Similarly, the casting form mandibular advancement incline 86 of the mandibular advancer $52^{ii}$, or the similarly contoured polymerized material 98 thereunder, disposed on the "b" side of the upper dental arch 26 cams relative to the crown mandibular advancement incline 112 of the mandibular advancer $52^i$ disposed on the "b" side of the lower arch 6 when disposed in interfacing relation therewith. Again, this may require the patient to "slide" his/her mandible 4 forward or mesially. This sliding movement is again facilitated by disposing the first section 70 of the casting form occlusal surface 66 in at least generally parallel relation with the occlusal plane of the upper dental arch 6 such that the crown occlusal surface 104 of the corresponding crown 102 may slide thereon to establish the noted camming engagement for affecting mesial mandibular movement.

In the configuration illustrated in FIG. 1A, the mandibular advancer $52^i$ includes only the crown 102 with its various features. A variation would be to use the crown 102 in combination with the casting form 54 discussed above in relation to the mandibular advancer $52^{ii}$, and in the generally same manner as will be discussed below in relation to the mandibular advancer $52^v$ of FIGS. 9–13. Generally, the crown 102 would be installed over a tooth in the subject dental arch in the above-described manner, and the casting form 54 would be disposed over the crown 102 and at least one additional tooth in the subject dental arch so as to dispose the casting form mandibular advancement incline 86 and crown mandibular advancement incline 112 at least generally proximate to each other and at least in generally parallel relation, and more preferably actually in interfacing relation. The flowable material would be cured with the crown 102 being within the casting form 54 to appropriately interconnect the same.

Figure 7:
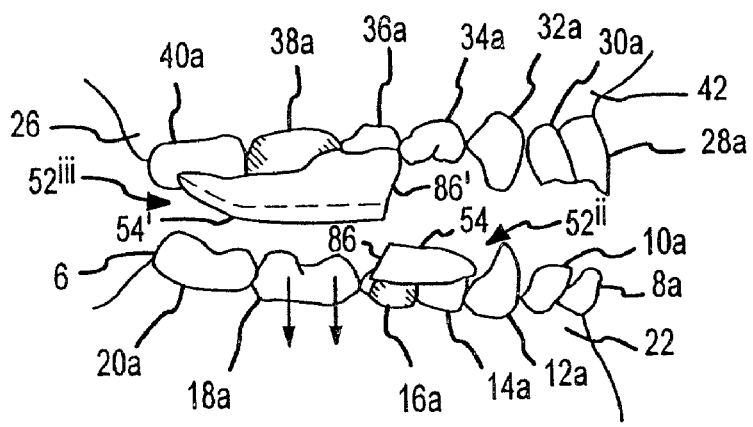
FIG. 7 is a cutaway side view of one side of upper and lower dental arches of a patient with another embodiment of a casting form mandibular advancer being installed on the upper dental arch and with the embodiment of the casting form mandibular advancer presented in FIG. 4 being installed on the lower dental arch.

Another embodiment of an mandibular advancer 52 is presented in FIG. 7. Referring now to FIG. 7, a mandibular advancer 52$^{ii}$ of the type discussed above is installed on each side of the lower dental arch 6. In this case, however, the corresponding casting forms 54 are installed over only two teeth within the lower dental arch 6, namely the lower first bicuspid 14 and the lower second bicuspid 16. Moreover, the casting form mandibular advancement incline 86 of each of these mandibular advancers 52$^{ii}$ is disposed to project at least generally distally, whereas in the configuration discussed above in relation to FIG. 1B the inclines 86 projected at least generally mesially.

A pair of mandibular advancers 52$^{iii}$ are installed on both sides of the upper dental arch 26 and as illustrated in FIG. 7. Each of these mandibular advancers 52$^{iii}$ includes a casting form 54' with polymerized material therein 98. A "prime" designation is used for the casting forms 54' of the mandibular advancers 52$^{iii}$ since they have a larger occlusal-gingival extent compared to the casting forms 54 used by the mandibular advancer 52$^{ii}$ (the dashed line in FIG. 7 representing the location of the casting form occlusal surface 66 of the casting form 54 of the mandibular advancer 52$^{ii}$). The mandibular advancers 52$^{iii}$ with their modified casting forms 54' generally address an "open bite" dental condition. Enhancement of the occlusal-gingival extent of the casting forms 54' causes their corresponding casting form occlusal surface 66' to engage their corresponding lower first molar 18 to at least reduce the potential for further eruption of the same (to resist further protrusion from the gingiva 22, and possibly even to force the lower first molar 18 in the direction of the pair of arrows presented in FIG. 7).

Figure 8:
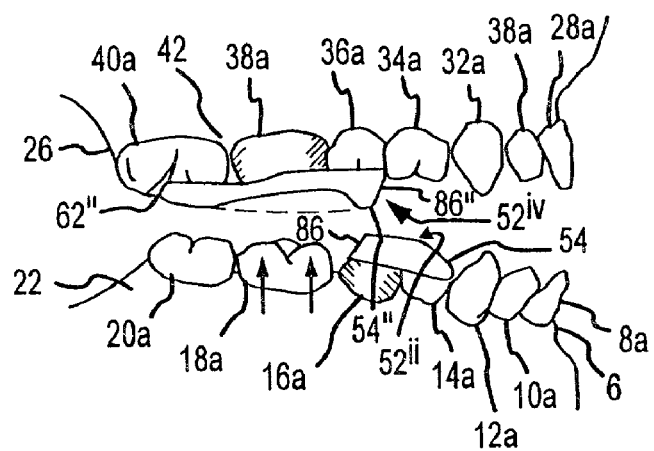
FIG. 8 is a cutaway side view of one side of upper and lower dental arches of a patient with another embodiment of a casting form mandibular advancer being installed on the upper dental arch and with the embodiment of the casting form mandibular advancer presented in FIG. 4 being installed on the lower dental arch.

Another embodiment of an mandibular advancer 52$^{iv}$ is presented in FIG. 8. Referring now to FIG. 8, a mandibular advancer 52$^{ii}$ of the type discussed above is installed on each side of the lower dental arch 6. In this case, however, the corresponding casting forms 54 are installed over only two teeth, namely the lower first bicuspid 14 and the lower second bicuspid 16. Moreover, the casting form mandibular advancement incline 86 of each of these mandibular advancers 52$^{ii}$ is disposed to project at least generally distally, whereas in the configuration discussed above in relation to FIG. 1B the inclines 86 projected at least generally mesially.

A pair of mandibular advancers 54$^{iv}$ are installed on both sides of the upper dental arch 26. Each of these mandibular advancers 52$^{iv}$ includes a casting form 54" with polymerized material therein 98. A "double prime" designation is used for the casting forms 54" on the upper dental arch 26 in the case of the mandibular advancers 52$^{iv}$ since they have a reduced occlusal-gingival extent compared to the casting forms 54 used by the mandibular advancer(s) 52$^{ii}$ (the dashed line in FIG. 8 representing the casting form occlusal surface 66 of the mandibular advancer 52$^{ii}$). More specifically, at least a portion of the casting form occlusal surface 66" is recessed or concave to least a certain degree. The mandibular advancers 52$^{iv}$ with their modified casting forms 54" generally address a "deep bite" dental condition. Reduction of the occlusal-gingival extent of the casting forms 54" allows for further eruption of their corresponding lower first molar 18 (i.e., it allows the lower first molars 18 to continue to advance from the gingiva 22 in the direction of the pair of arrows illustrated in FIG. 8).

Figure 12:
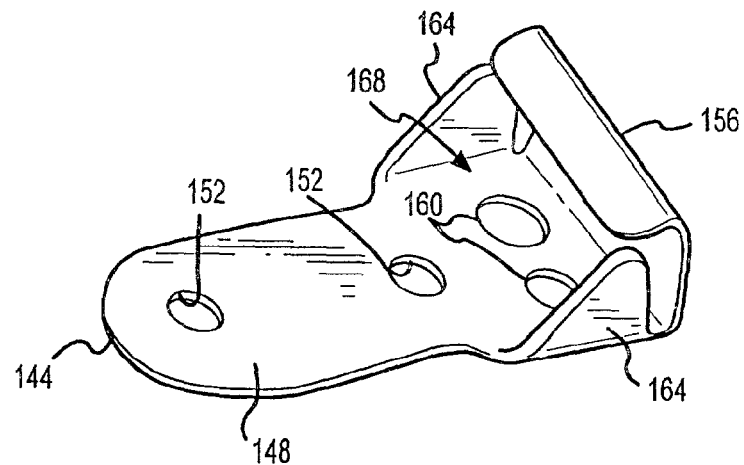
FIG. 12 is a perspective view of the crown mandibular advancement incline frame from the crown assembly of FIG. 10.
Figure 13:
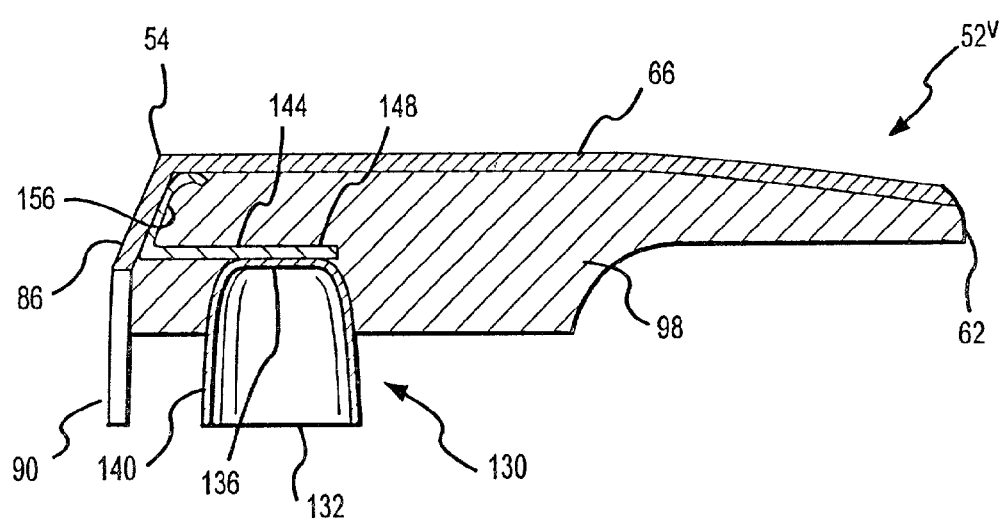
FIG. 13 is a cross-sectional view of the embodiment of the combination casting form/crown mandibular advancer presented in FIG. 9.

Another embodiment of an mandibular advancer 52, including the individual components thereof, is illustrated in FIGS. 9–13. The mandibular advancer 52$^{v}$ of FIGS. 9–13 includes a casting form 54 of the type discussed above in relation to the mandibular advancer 52$^{ii}$. Polymerized material 98 of the above-described type is also included within the casting form 54 of the mandibular advancer 52$^{v}$ (FIG. 13). The mandibular advancer 52$^{v}$, however, also includes a crown assembly 130 which is disposed within the repository 88 of the casting form 54. Various benefits are associated with including the crown assembly 130 within the casting form 54, including enhancing the "robustness" of the interconnection of the mandibular advancer 52$^{v}$ with the subject dental arch and enhancing the strength of the surface of the mandibular advancer 52$^{v}$ which "cams" to affect mandibular advancement.

The crown assembly 130 generally includes an crown 132 and a crown mandibular advancement incline frame 144 which is separately attached thereto. The crown 132 generally includes a crown occlusal surface 136 and an annular crown skirt 140 which extends away from the crown occlusal surface 136 and toward the patient's gingiva when the crown 132 is disposed over a tooth in the subject dental arch. The crown occlusal surface 136 is a flat, planar surface. Conventional crowns typically include an undulating occlusal surface to at least generally replicate the occlusal surface of the underlying tooth. Therefore, the configuration of the crown 132 is itself a significant departure from conventional crown designs. However, the crown 132 may still formed from materials used in conventional crowns, such as stainless steel, titanium, gold, and aluminum.

The crown mandibular advancement incline frame 144 is attached to the crown occlusal surface 136 of the crown 132. Preferred materials for the crown mandibular advancement incline frame 144 include metals such as stainless steel and titanium. Appropriate attachment techniques thereby include possibly spot welding, although brazing is presently preferred.

Components of the crown mandibular advancement incline frame 144 include a first frame section 148 and a second frame section 156. The second frame section 156 is preferably integrally formed with the first frame section 148 (i.e., formed from the same piece of material such that there is no joint of any kind therebetween). An acute angle (i.e., less than 90 degrees) exists between the first frame section 148 and the second frame section 156, and in one embodiment this angle is about 70 degrees. As such, the second frame section 156 is disposed at an angle of about 20 degrees relative to vertical, or the same as the angular disposition of the casting form mandibular advancement incline 86 of the casting form 54 as noted above. Therefore, the second frame section 156 may also be characterized as the crown mandibular advancement incline 156. The second frame section 156 may also actually define the "active" surface of the mandibular advancer 52$^{v}$ should the material of the casting form mandibular advancement incline 86 "wear away" during treatment.

Polymerized material 98 exists within the casting form 54 of the mandibular advancer 52$^{v}$ as will be discussed in more detail below. Certain features are incorporated in the crown assembly 130 to enhance one or more aspects of this polymerized material 98. For instance, a pair of first apertures 152 are disposed in that portion of the first frame section 148 which overlies the crown occlusal surface 136 of the crown 132. Polymerized material 98 preferably occupies the entire extent of these apertures 152 to improve the "interlock" between the crown assembly 132 and casting form 54 of the mandibular advancer 52$^{v}$. Another pair of apertures 160 are included in that portion of the first frame section 148 which extends beyond the "oval" of the crown 132 (i.e., beyond the crown skirt 140) and which are illustrated in FIG. 12. These particular apertures 160 facilitate the inclusion of polymerized material 98 between the crown skirt 140 and the first end 58 of the casting form 54 as illustrated in FIG. 13. Polymerized material 98 also supports the second frame section 156 in the noted angular position relative to the first frame section 148. In this regard, polymerized material 98 preferably occupies the entire extent of a pocket 168 which is defined by the first frame section 148, the second frame section 156, and a pair of extensions 164 which project from the first frame section toward, but not to, the apex of the second frame section 156. This "apex" of the second frame section 156 includes a rounded section by including a curl on the free end of the second frame section 156.

The mandibular advancer 52$^v$ of FIGS. 9–13 is installed on the patient generally in the same manner discussed above with regard to the mandibular advancer 52$^{ii}$ of FIGS. 1B and 4. There are of course some variations due to the inclusion of the crown assembly 130. Consider the case where a stone casting is made of the upper dental arch 26 for purposes of assembling the mandibular advancer 52$^v$. Here the crown 132 is disposed over a single tooth within the upper dental arch 26 (e.g., the upper second bicuspid 36) and properly fitted to the corresponding gingiva (e.g., via a trimming of the crown skirt 140 in a manner known in the art) before the casting form 54 with the flowable material therein is disposed over the upper dental arch 26 in generally the above-described manner. Moreover, the crown mandibular advancement incline frame 144 is placed into the desired position on the crown occlusal surface 136 before the casting form 54 with the flowable material therein is disposed over the upper dental arch 26 in generally the above-described manner. Typically this position will then be marked on the crown occlusal surface 136 such that the attachment of the crown mandibular advancement incline frame 144 to the crown 132 may be affected while off of the stone casting of the upper dental arch 26. However, it may be possible to attach the crown mandibular advancement frame incline frame 144 to the crown 132 while still on the stone casting. In any case, the crown 132 is removed from the stone casting of the upper dental arch 26 so that the release agent may be disposed on appropriate portions of the upper dental arch 26 in the above-noted manner and for the above-noted purposes. In this regard and with the crown mandibular advancement incline frame 144 then being appropriately fixed to the crown 132 in the desired position, the crown 132 is disposed over the desired tooth within the upper dental arch 26 (e.g., the upper second bicuspid 36). Then the casting form 54 with the flowable material therein is disposed over the crown assembly 130, as well as at least one other tooth of the upper dental arch 26. Again, typically the casting form 54 will be disposed over the entirety of at least two teeth in a given dental arch, and at least part of a third tooth (e.g., the second molar). In the illustrated embodiment, the casting form 54 of the mandibular advancer 52$^v$ will be disposed over the entirety of the upper second bicuspid 36 (although the crown assembly 130 is of course disposed therebetween), the upper first molar 38, and part of the upper second molar 40. Completion of the installation of the mandibular advancer 52$^v$ thereafter proceeds at least generally in accordance with the protocol set forth above for the mandibular advancer 52$^{ii}$.

Figure 14:
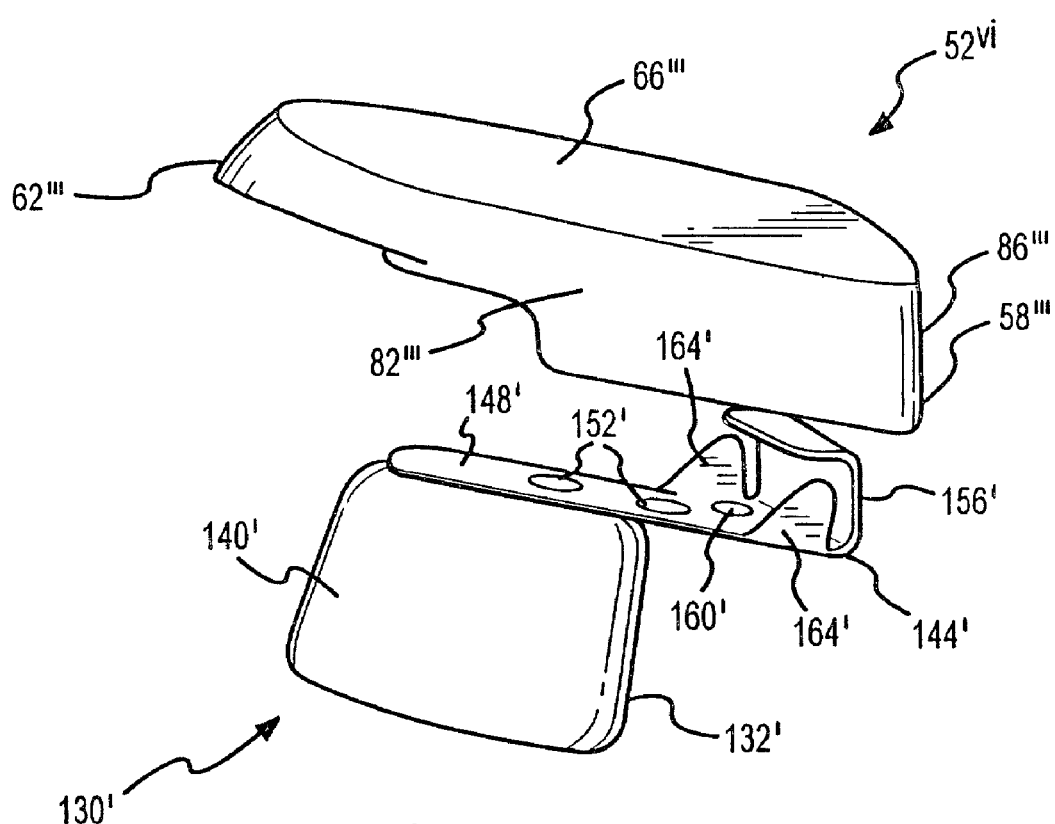
FIG. 14 is an exploded, perspective view of another embodiment of a combination casting form/crown mandibular advancer.

Another embodiment of an mandibular advancer is presented in FIG. 14, and which is fundamentally the same as the mandibular advancer 52$^v$ of FIGS. 9–13 discussed above. Similar components are thereby similarly numbered, but a "single prime" designation is used in relation to the crown assembly 130 and a "triple prime" designation is used in relation to the casting form 54. The mandibular advancer 52$^{vi}$ generally utilizes a crown mandibular advancement incline frame 144' having a longer first frame section 148' so as to dispose the second frame section 156' further from the tooth-long axis of the tooth over which the crown 132' is disposed. Note that one of the apertures 152' is now disposed beyond the crown skirt 140'. Another difference is that the casting form lingual skirt 82''' and the casting form buccal skirt 78''' (not shown) have a larger occlusal-gingival extent than in the case of the casting form 54. Otherwise, the casting form mandibular advancer 54$^{vi}$ is substantially the same as the mandibular advancer 52$^v$.

Figure 15:
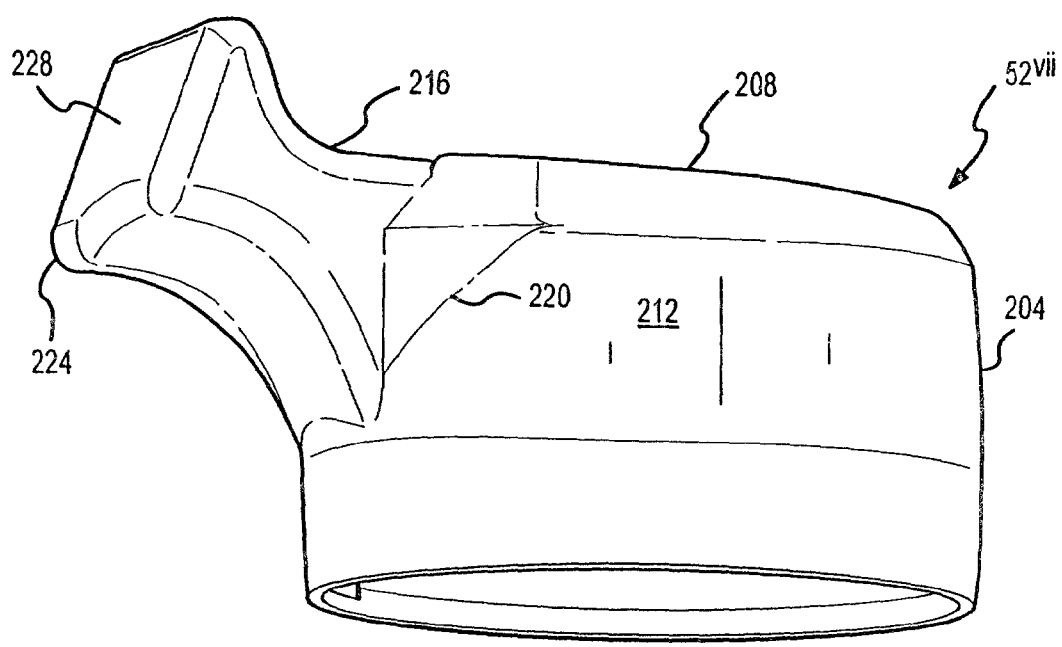
FIG. 15 is a perspective view of another embodiment of a crown mandibular advancer.

Another embodiment of an mandibular advancer 52 is presented in FIG. 15. The mandibular advancer 52$^{vii}$ of FIG. 15 includes a crown 204 which has a crown occlusal surface 208 and a crown skirt 212 which extends from the crown occlusal surface 208 and toward the patient's gingiva when the crown 204 is disposed over a particular tooth in the subject dental arch. The profile of the crown occlusal surface 208 may be contoured in the manner of conventional crowns, or may be flat as described above in relation to the crown 132 used by the mandibular advancer 52$^v$ of FIGS. 9–13.

The crown 204 further includes an extension 216 which projects away from the crown skirt 212 along a direction which is at least generally parallel with the mesio-distal direction when the crown 204 is installed over a tooth. Preferably the crown occlusal surface 208, the crown skirt 212, and the extension 216 are integrally formed (i.e., formed from a single piece of material such that there is no joint of any kind therebetween). The extension 216 includes a skirt end 220 and a free end 224 on which is disposed a crown mandibular advancement incline 228 which defines the active surface of the mandibular advancer 52$^{vii}$. As such, the crown mandibular advancement incline 228 is disposed beyond the "oval" of the crown 204 (i.e., beyond the crown skirt 212).

Various techniques may be used to integrally form the extension with the crown skirt 212 and/or crown occlusal surface 208, including hydroforming or explosive forming techniques which produce a hollow extension 216. In this case, any number of standard chemically polymerizing dental and orthodontic adhesive systems may be used to fixedly mount the crown 204 over/onto the desired tooth. These types of materials are sufficiently rigid when cured to enhance the support of the crown mandibular advancement incline 228. That is, an amount of orthodontic bonding system material may be positioned within the crown 204 before installing the same over the tooth such that the entirety of the hollow interior of the extension 216 is occupied by this orthodontic bonding system material when the crown 204 is installed over the subject tooth. Alternatively, the hollow interior of the extension 216 may remain "unoccupied" when the crown 214 is mounted on the subject tooth.

Another technique which may be used to form the crown 204 in an integral fashion would entail having a mold in the shape of the crown 204, and which included a spacer or the like disposed within the mold. When this spacer was removed, the remaining space would define the hollow interior for the crown skirt 212. In this case the extension 216 would be solid and integrally formed with a solid upper portion of the crown 204 (e.g., the "upper" portion of the crown 204 which includes the crown occlusal surface 208), as well as the crown skirt 212. Vacuum-forming techniques could also be employed to define an integral plastic crown 204 with a hollow extension 216. Those materials noted above relating to the crown 102 may be used for the crown 204 in this instance.

The configuration of the crown 204 could be realized by a non-integral construction as well (i.e., such that there was at least one joint in the structure of the crown 204). For instance, the above-noted spacer could be replaced with a body having an occlusal surface and an annular skirt. In this case, the upper portion of the materials that were being molded would not only define the extension 216 in a solid form, but would also extend over the occlusal surface of this crown body and interconnect with the same. At least a portion of the crown skirt 212 would then be defined by this hollow body.

In the configuration illustrated in FIG. 15, the mandibular advancer $52^{vii}$ includes only the crown 204 with its various features. A variation would be to use the crown 204 in combination with the casting form 54 discussed above in relation to the mandibular advancer $52^{ii}$, and in the generally same manner as will be discussed above in relation to the mandibular advancer $52^v$ of FIGS. 9–13. Generally, the crown 204 would be installed over a tooth in the subject dental arch in the above-described manner, and the casting form 54 would be disposed over the crown 204 and at least one additional tooth in the subject dental arch so as to dispose the casting form mandibular advancement incline 86 and crown mandibular advancement incline 228 at least generally proximate to each other and at least in generally parallel relation, and more preferably in interfacing relation. The flowable material would be cured with the crown 204 being within the casting form 54 to appropriately interconnect the same.

Figure 16:
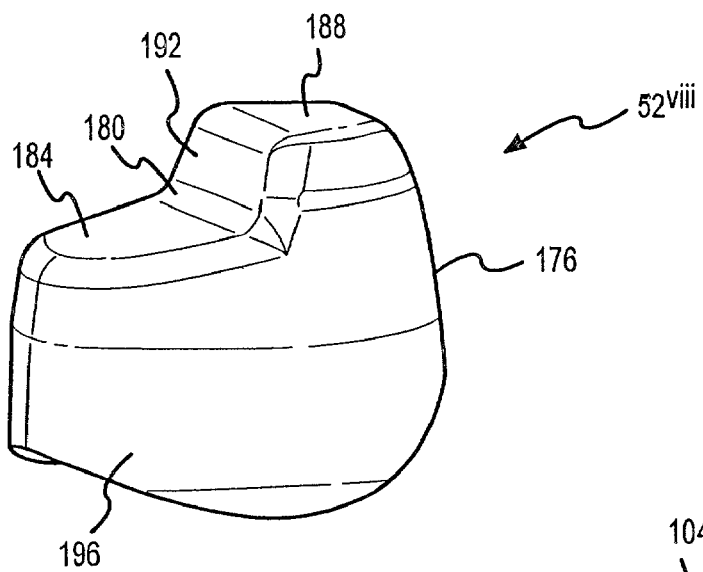
FIG. 16 is a perspective view of another embodiment of a crown mandibular advancer.

Another embodiment of an mandibular advancer 52 is presented in FIG. 16. The mandibular advancer $52^{viii}$ of FIG. 16 includes a crown 176. The crown 176 has a crown occlusal surface 180 and the crown skirt 196 which extends from the crown occlusal surface 180 and toward the patient's gingiva when the crown 176 is disposed over a particular tooth in a given dental arch. The crown occlusal surface 180 includes a first occlusal section 184 and a second occlusal section 188 which are disposed at different elevations. As such, when the crown 176 is disposed over a given tooth within a particular dental arch, the second occlusal section 188 is disposed further from the occlusal plane associated with this particular dental arch than the first occlusal section 184. Both the first occlusal section 184 and the second occlusal section 188 are at least generally flat, planar surfaces, and in one embodiment are disposed at least substantially parallel with the occlusal plane of the dental arch on which the crown 176 is installed over one of its corresponding teeth.

A crown mandibular advancement incline 192 extends between and interconnects the first occlusal section 184 and the second occlusal section 188 of the crown 176, and defines the "active" surface of the mandibular advancer $52^{viii}$. As such, the crown mandibular advancement incline 192 is also part of the crown occlusal surface 180 and is disposed at somewhat of a "mid" portion thereof (e.g., it is disposed closer to a central axis which corresponds with a tooth-long axis of a tooth over which the crown 176 is disposed, than to the crown skirt 196). The materials noted above in relation to the crown 102 may be used for the crown 176 as well.

Figure 17A:
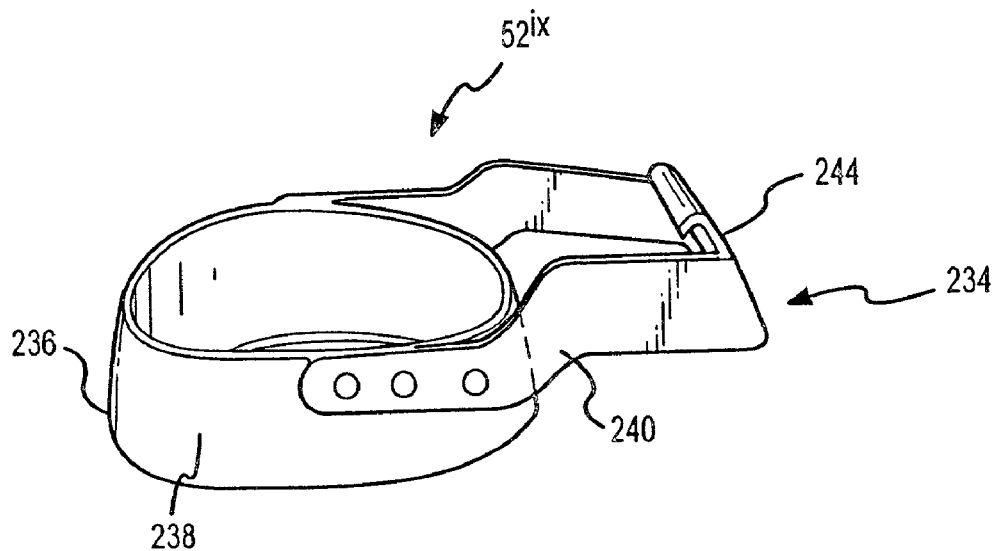
FIG. 17A is a perspective view of an embodiment of a band mandibular advancer.
Figure 17B:
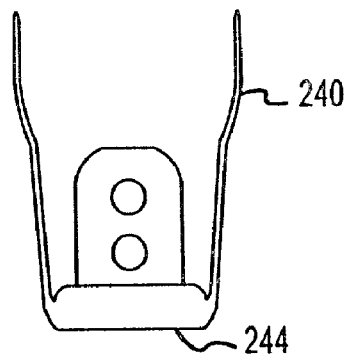
FIG. 17B is a top view of the band mandibular advancement incline frame used by the band mandibular advancer presented in FIG. 17A.
Figure 18:
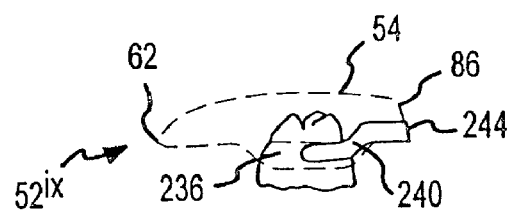
FIG. 18 is a side view of the embodiment cf the band mandibular advancer presented in FIG. 17A, when installed on a tooth.

Another embodiment of an mandibular advancer 52 is presented in FIGS. 17A–B and 18. The mandibular advancer $52^{ix}$ of FIGS. 17A–B and 18 includes a band assembly 234. The band assembly 234 in turn includes a band 236 which is defined by an annular skirt 238 which may be disposed circumferentially about a particular tooth within the desired dental arch. A band mandibular advancement frame 240 is attached to this band 236 on generally the buccal and lingual sides thereof (e.g., spot welding, brazing). Disposed on the free end of the band mandibular advancement frame 240 is a band mandibular advancement incline 244 and which defines the "active" surface for the mandibular advancer $52^{ix}$.

In the configuration illustrated in FIGS. 17A–B and 18, the mandibular advancer $52^{ix}$ includes only the band assembly 234 with its various features. A variation would be to use the band assembly 234 in combination with the casting form 54 discussed above in relation to the mandibular advancer $52^{ii}$, and in the generally same manner as discussed above in relation to the mandibular advancer $52^v$ of FIGS. 9–13. Generally, the band assembly 234 would be installed around a tooth in the subject dental arch in the above-described manner, and the casting form 54 would be disposed over the band assembly 234 and at least one additional tooth in the subject dental arch so as to dispose the casting form mandibular advancement incline 86 and band mandibular advancement incline 244 at least generally proximate to each other and at least in generally parallel relation, and more preferably in interfacing relation. The flowable material would be cured with the band assembly 234 being within the casting form 54 to appropriately interconnect the same.

Another embodiment of a mandibular advancer 52 which may be used by the mandibular advancement system 50 is presented in FIGS. 19 and 20A–B. The mandibular advancer $52^x$ of FIGS. 19 and 20A–B includes a crown 252 which is installed over a tooth in the subject dental arch. Typically the mandibular advancer $52^x$ will be incorporated into a mandibular advancement system 50 by being installed on both sides of both the upper dental arch 24 and the lower dental arch 6 (FIGS. 1A–B), typically on both of the upper first molars 38 and on both of the lower first molars 18. The crown 252 generally includes a crown occlusal surface 256 and an annular crown skirt 264 which extends away from the crown occlusal surface 256 and toward the corresponding gingiva when the crown 252 is installed over a tooth within a given dental arch.

A crown mandibular advancement incline 260 defines at least substantially the entirety of, and more preferably the entirety of, the crown occlusal surface 256 of the crown 252, and is the "active" surface of the mandibular advancer $52^x$. Generally the crown mandibular advancement incline 260 occupies/extends along the entire mesio-distal extent of the crown 252. Like the other mandibular advancement inclines described herein, the crown mandibular advancement incline 260 is preferably an at least substantially flat, planar surface. However, the orientation of the crown mandibular advancement incline 260 relative to the corresponding occlusal plane differs from the orientation of the other mandibular advancement inclines addressed herein. The crown mandibular advancement incline 260 assumes an orientation which is more flat than the mandibular advancement inclines discussed above. In one embodiment, the crown mandibular advancement incline 260 is disposed at an angle of no more than about 20° relative to horizontal or to a plane which is parallel with the occlusal of the subject dental arch (e.g., more than about 70° relative to vertical), and is more preferably disposed at an angle of about 16° relative to horizontal or a plane which is parallel with the occlusal of the subject dental arch. This orientation of the crown mandibular advancement incline 260 provides the advantage of providing positive forward/rearward guidance to the mandible 4 of a patient, while the increased length (measured mesio-distally) of the incline 260 significantly reduces the potential for becoming disengaged with the active surface of the mandibular advancer 52 disposed on the opposite dental arch. That is, the patient should not be able to move his/her mandible 4 to a position where the crown mandibular advancement inclines 260 on the patient's upper dental arch 260 will become disengaged with the corresponding crown mandibular advancement inclines 260 on the patient's lower dental arch 6.

With the crown mandibular advancement incline 260 being on and in fact defining at least substantially the entirety of the crown occlusal surface 256, the crown 252 is "taller" than conventional crowns. When the crown 252 is installed over the desired tooth, there is a space between the occlusal surface of this tooth and the crown occlusal surface 256. In one embodiment, the minimum vertical extent of this space is about 2 mm at the apex of the crown mandibular advancement incline 260, and may be as much as about 3.5 mm at the apex of the crown mandibular advancement incline 260 (measured relative to the occlusal-most surface of the corresponding tooth). A suitable orthodontic bonding system may be used to fixedly mount the crown 252 over/onto the subject tooth. These types of materials are sufficiently rigid when cured to enhance the support of the crown mandibular advancement incline 260. That is, an amount of orthodontic bonding system material may be positioned within the crown 252 before installing the same over the subject tooth such that the entirety of the space between the crown 252 and the corresponding tooth is occupied by this orthodontic bonding system material when the crown 252 is installed over the subject tooth. Alternatively, the space may remain as an "air gap" between the crown occlusal surface 256 and the occlusal surface of the tooth on which the crown 252 is mounted.

The existence of the above-noted space facilitates the dispositioning of the crown mandibular advancement incline 260 in a desired position when installed over its corresponding tooth (e.g., disposed at an angle of no more than about 20 degrees relative to a plane which is parallel with the occlusal of the dental arch having the tooth over which the crown 252 is installed). In this regard, the gingival-most extreme of the crown mandibular advancement incline 260 initiates where the tip of the corresponding tooth begins to extend inwardly toward its tooth-long axis and is disposed in at least generally parallel relation therewith. The incline 260 continues to extend occlusally beyond the occlusal surface of this tooth. In one embodiment, the length of the crown mandibular advancement incline 260 is within a range of about 8 mm to about 12 mm (measured parallel to the incline 260), the width of the crown mandibular advancement incline 260 is within a range of about 5 mm to about 9 mm, and/or has an area within a range of about 40 mm$^2$ to about 108 mm$^2$. Therefore, the surface area of the crown mandibular advancement incline 260 is larger than the surface area of other inclines addressed herein. This larger surface area of the crown mandibular advancement incline 260 again provides the advantage of reducing the potential, and in all likelihood eliminating, the potential that the inclines 260 disposed on the upper dental arch 26 of the patient will become disengaged with their corresponding incline 260 disposed on the lower dental arch 6 of the patient.

The crown occlusal surface 256, the crown mandibular advancement incline 260, and the crown skirt 264 are integrally formed, similar to the crown 102 of FIGS. 5–6. Stated another way, the crown occlusal surface 256, the crown mandibular advancement incline 260, and crown skirt 264 are formed from a single piece of material such that there is no joint of any kind between any of these components. Materials which are commonly used to make conventional crowns may be used to make the crowns 252 here as well, such as stainless steel, titanium, gold, and aluminum. Other materials such as vacuum-formed plastics such as polycarbonate, acrylic, styrene, buturate, and vinyls may be used as well for the crowns 252.

There are a number of benefits associated with the crown 252. One is its relative simplicity of manufacture since it is integrally formed and due to the configuration/orientation of the crown mandibular advancement incline 260. Another is that its crown mandibular advancement incline 260 facilitates the use of the crown 252 on the patient's first molars (both upper and lower as noted above). FIGS. 20A–B each show an orientation to affect mesial advancement of the patient's mandible, with the arrow 268 being pointed in the mesial direction. The first molars provide a strong and sturdy anchorage for the types of forces encountered when affecting the type of mandibular advancement treatment addressed herein. Moreover, the first molars come into the mouth when the patient is about 6 years of age, so the mandibular advancers 52$^x$ may be used on very young patients. Finally, using the crowns 252 in a mandibular advancement system 50 alleviates the need for a mandibular advancement incline which is "mesially extended" for the two mandibular advancers 52 used on the patient's upper dental arch 26.

The crown 252 with its various features may define the entirety of the mandibular advancer 52$^x$ as described above. A variation would be to use the crown 252 in combination with the casting form 54 discussed above in relation to the mandibular advancer 52$^{ii}$, and in the generally same manner as discussed above in relation to the mandibular advancer 52$^v$ of FIGS. 9–13. Generally, the crown 252 would be installed over a tooth in the subject dental arch in the above-described manner, and the casting form 54 would be disposed over the crown 252 and at least one additional tooth in the subject dental arch so as to dispose the casting form mandibular advancement incline 86 and crown mandibular advancement incline 260 at least generally proximate to each other and at least in generally parallel relation, and more preferably actually in interfacing relation. The flowable material would be cured with the crown 252 being within the casting form 54 to appropriately interconnect the same.

Figure 21:
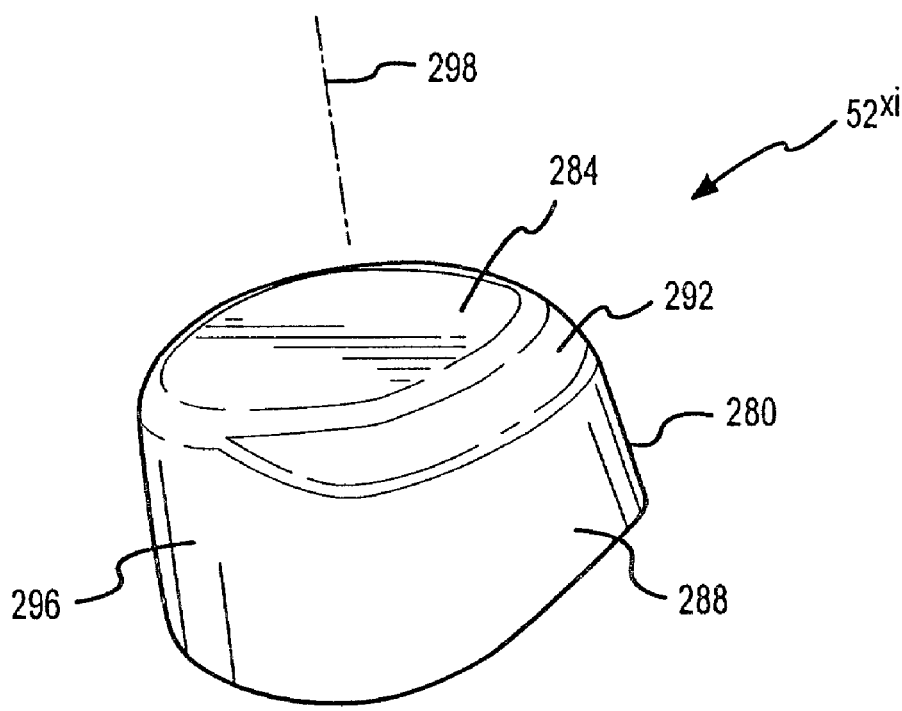
FIG. 21 is a perspective view of another embodiment of a crown mandibular advancer.
Figure 22:
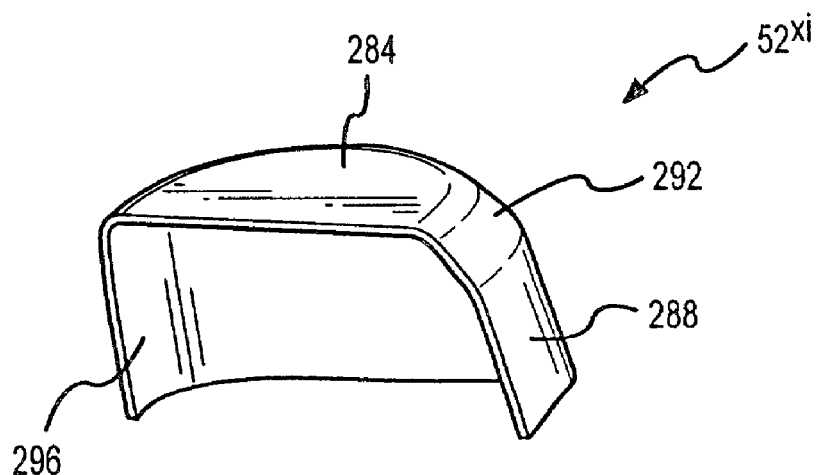
FIG. 22 is a cutaway view of the crown mandibular advancer of FIG. 21.

Another embodiment of an mandibular advancer 52 which may be used by the mandibular advancement system 50 is presented in FIGS. 21–22. The mandibular advancer 52$^{xi}$ of FIGS. 21–22 includes a crown 280 which is installed over a tooth in the subject dental arch. The crown 280 generally includes a crown occlusal surface 284 and an annular crown skirt 296 which extends away from the crown occlusal surface 284 and toward the corresponding gingiva when the crown 280 is installed over a tooth within a given dental arch. The shape of the crown occlusal surface 284 should not significantly affect the generation of mandibular treatment forces by the crown 280. Therefore, any shape/configuration may be utilized for the crown occlusal surface 284, including being at least substantially flat or planar as shown, and preferably at least generally in parallel relation with the occlusal of the corresponding dental arch, as well as being contoured to least generally approximate the occlusal anatomy of the tooth on which the crown 280 is installed (not shown).

A crown mandibular advancement incline 292 is disposed on an "end" 288 of the crown 280 which will be either mesially or distally disposed when the crown 280 is installed on a tooth in the subject dental arch and further depending upon the desired directional movement of the mandible 4. The crown mandibular advancement incline 292 would be disposed on the distal if the crown 280 is installed on a tooth in the lower dental arch 6 (i.e., be distally disposed) to affect mandibular advancement, and would be disposed on the mesial if the crown 280 is installed on a tooth in an upper dental arch 26 (i.e., be mesially disposed) to affect mandibular advancement. The "active" surface of the mandibular advancer $52^{xi}$ is the crown mandibular advancement incline 292, and in one embodiment this incline 292 curves at least generally about a reference axis 298 which is a least generally parallel with a tooth-long axis of the tooth on which the crown 280 is installed. This is one distinction between the orthodontic mandibular advancer $52^{xi}$ of FIGS. 21–22 and the orthodontic mandibular advancer $52^{i}$ of FIGS. 5–6 as described above where it's crown mandibular advancement incline 112 was characterized as being an at least substantially flat, planar surface.

As in at least some of the above-noted cases where crowns have been described for use in relation to movement of the mandible 4, the crown 280 may be used alone to function as a mandibular advancer 52, or may be disposed withing a casting form 54 to define an assembly for a mandibular advancer 52.

Figure 23:
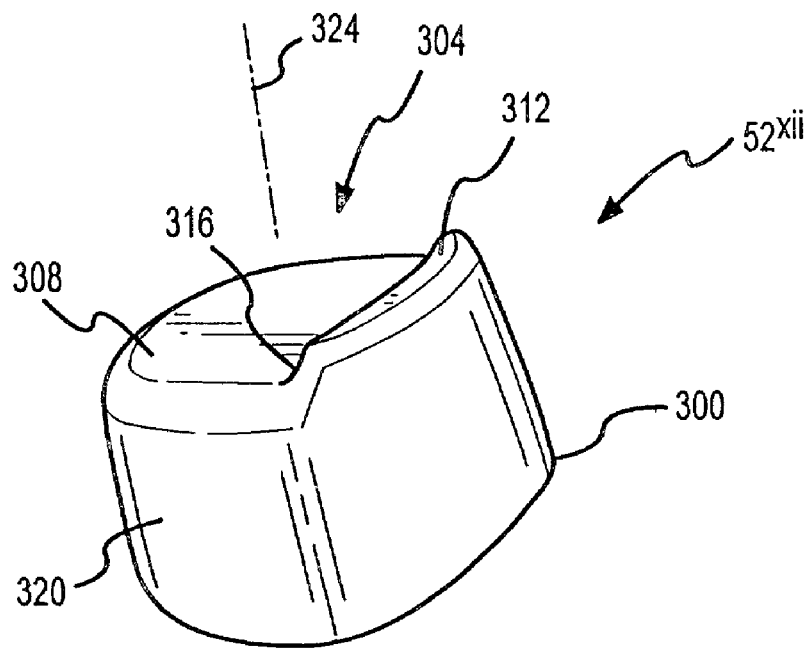
FIG. 23 is a perspective view of another embodiment of a crown mandibular advancer.
Figure 24:
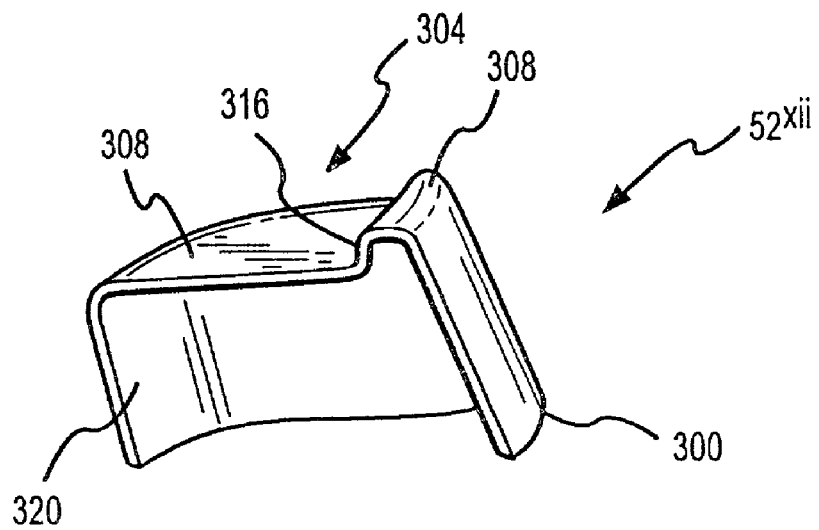
FIG. 24 is a cutaway view of the crown mandibular advancer of FIG. 23.

Another embodiment of an mandibular advancer 52 is presented in FIGS. 23–24. The mandibular advancer $52^{xii}$ of FIGS. 23–24 includes a crown 300. The crown 300 has a crown occlusal surface 304 and a crown skirt 320 which extends from the crown occlusal surface 304 and toward the patient's gingiva when the crown 300 is disposed over a particular tooth in a given dental arch. The crown occlusal surface 304 includes a first occlusal section 308 and a second occlusal section 312 which are disposed at different elevations or in vertically-spaced relation. As such, when the crown 300 is disposed over a given tooth within a particular dental arch, the second occlusal section 312 is disposed further from the occlusal plane associated with this particular dental arch than the first occlusal section 308. The shape of the first occlusal section 308 and the shape of the second occlusal section 312 should not affect the generation of mandibular movement treatment forces by the crown 300. Therefore, any shape/configuration may be utilized for both the first and second occlusal sections 308, 312, including being at least substantially flat or planar, and preferably in at least generally parallel relation with the occlusal of the corresponding dental arch, as well as being contoured to at least generally approximate the occlusal anatomy of the tooth on which the crown 300 is mounted (not shown). In those cases where the crown mandibular advancement incline 316 of the crown 300 is disposed on the extreme mesial or distal end of the crown 300 as shown in FIGS. 23–24, the second occlusal section 312 will be of such a reduced mesio-distal extent that the same will typically be at least generally convexly-shaped (e.g., in effect defined by a radius), and will likely be of insufficient mesio-distal extent to approximate any occlusal anatomy of a tooth.

The crown mandibular advancement incline 316 of the crown 300 of FIGS. 23–24 extends between and interconnects the first occlusal section 308 and the second occlusal section 312 of the crown 300, and defines the "active" surface of the mandibular advancer $52^{xii}$ in relation to the generation of forces for affecting movement of the mandible 4. As such, the crown mandibular advancement incline 316 is also part of the crown occlusal surface 304 and is disposed at an intermediate portion thereof (e.g., somewhere between the mesial and distal extremes of the crown 300 when installed on a particular tooth). Therefore and in at least this respect, the crown 300 of FIGS. 23–24 is at least generally similar to the crown 176 described above in relation to FIG. 16. There are, however, differences between these two embodiments. One is that the crown mandibular advancement incline 316 of the crown 300 of FIGS. 23–24 curves at least generally about a reference axis 324 which is a least generally parallel with a tooth-long axis of the tooth on which the crown 300 is installed, whereas the crown mandibular advancement incline 196 of the crown 176 was noted above to be at least substantially flat or planar. Another distinction is the location of the crown mandibular advancement incline 316. In the case of the crown 300, its crown mandibular advancement incline 316 is disposed closer to its mesial or distal extreme of the crown 300 than the crown mandibular advancement incline 192 of the crown 176 of FIG. 16. Generally, the crown 300 in the form illustrated in FIGS. 23–24 will typically be utilized for a rather significant Class II malocclusion where the patient's mandible 4 is rather significantly retracted. In this case, the crown 300 will typically be mounted on a lower first molar 18 and with the incline 316 being disposed at least generally proximate the mesial end of the crown 300. Stated another way, the crown mandibular advancement incline 316 will project at least generally distally.

For those cases where a mandibular advancement crown includes a crown mandibular advancement incline on its crown occlusal surface (e.g., crown 176 of FIG. 16, crown 300 of FIGS. 23–24), this crown mandibular advancement incline may actually be disposed at any mesial-distal location or position on its corresponding crown occlusal surface. It should be appreciated that there will be some limit as to how close such a crown mandibular advancement incline may be disposed to the mesial or distal extreme of the crown. Generally and in relation to the crown 300 of FIGS. 23–24, the minimum mesio-distal extent of the second occlusal section 312 will be approximately twice the wall thickness of the material which has been used to form the crown 300.

Figure 25:
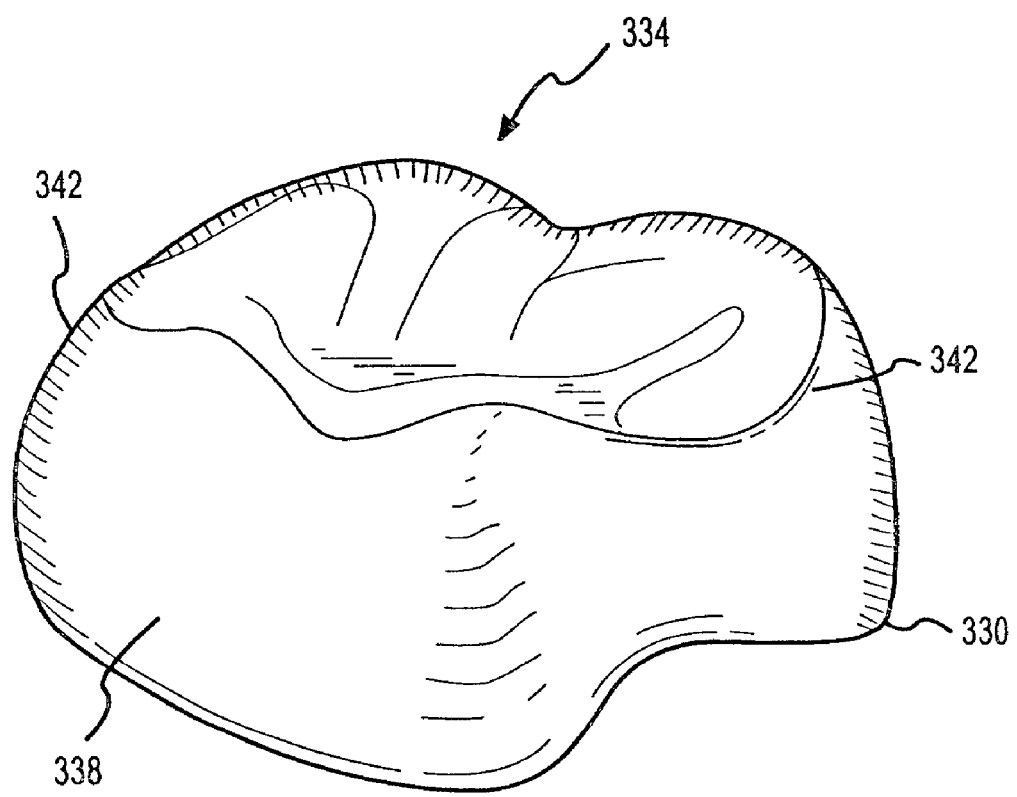
FIG. 25 is a perspective view of a crown having an enhanced occlusal-gingival extent.

FIG. 25 illustrates a crown 330. The crown 330 has what may be characterized as a conventional crown occlusal surface 334 (i.e., contoured to least generally approximate the occlusal anatomy of the tooth on which the crown 330 is mounted or installed), and a crown skirt 338 which extends from the crown occlusal surface 334 and toward the patient's gingiva when the crown 330 is disposed over a particular tooth in a given dental arch. There are at least two applications contemplated for the crown 330. Both of these applications entail mounting the crown 330 on a tooth in a given dental arch such that it has a "higher" profile than conventional crowns (e.g., mounted more "proudly" on the subject tooth). That is, the crown 330 is installed on the desired tooth such that a space exists between the occlusal surface of the tooth and the interior of the crown occlusal surface 334 of the crown 330 as will be discussed in more detail below. The shape of the crown occlusal surface 334 should not significantly affect the functionality of the crown 330 for either of the applications currently contemplated for the crown 330 and which will be addressed below. Therefore, any shape/configuration may be utilized for the crown occlusal surface 334, including being at least substantially flat or planar, and preferably in at least generally parallel relation with the occlusal of the corresponding dental arch (not shown), as well as being contoured to at least generally approximate the occlusal anatomy of the tooth on which the crown 300 is mounted and as illustrated in FIG. 25.

One application for the crown 330 is as a mandibular advancer 52. Activating forces for affecting movement of the mandible 4 in this case are realized through a transition 342 which is disposed between the crown occlusal surface 334 and the annular crown skirt 338, and which thereby functions as a crown mandibular advancement incline in accordance with the foregoing. This transition 342 has a generally arcuate and somewhat of a convex shape. Another application for the crown 330 is for providing additional occlusal support during movement of the patient's mandible 4. More specifically, the crowns noted above which have at least some type of "active" surface for affecting/retaining mandibular movement/position may be "taller" than conventional crowns (i.e., such that there is a space between the occlusal surface of the tooth and the interior of the crown occlusal surface). As such, the patient's jaw is retained in a somewhat more "open" position when these active surfaces are engaging or are fulling engaged. Installing at least one or more crowns 330 on each side of the patient's upper dental arch 26 and/or lower dental arch 6 may be utilized to provide additional occlusal support for the patient in these instances, provided these crowns 330 also have an enhanced gingival-occlusal extent and/or such that there is a space between the occlusal surface of the tooth and the interior of the crown occlusal surface 334.

Figure 26:
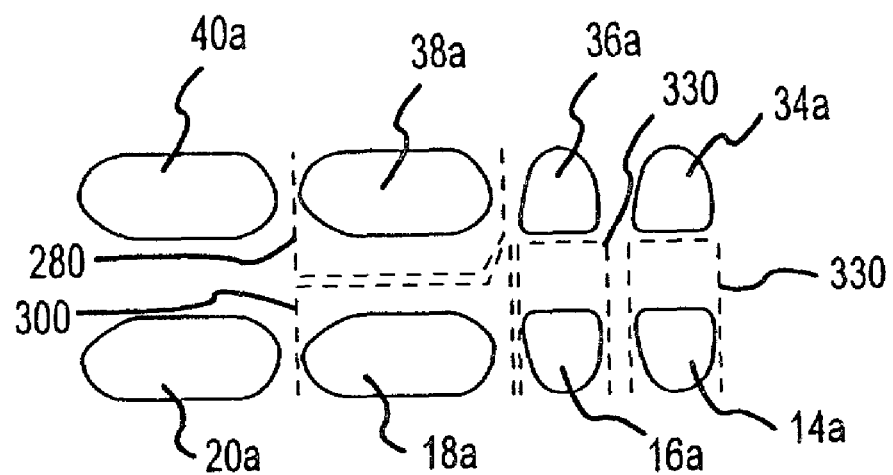
FIG. 26 is a cutaway side view of one side of upper and lower dental arches of a patient with one configuration of crown-based mandibular advancers and the crown of FIG. 25 for providing enhanced occlusal support.
Figure 27:
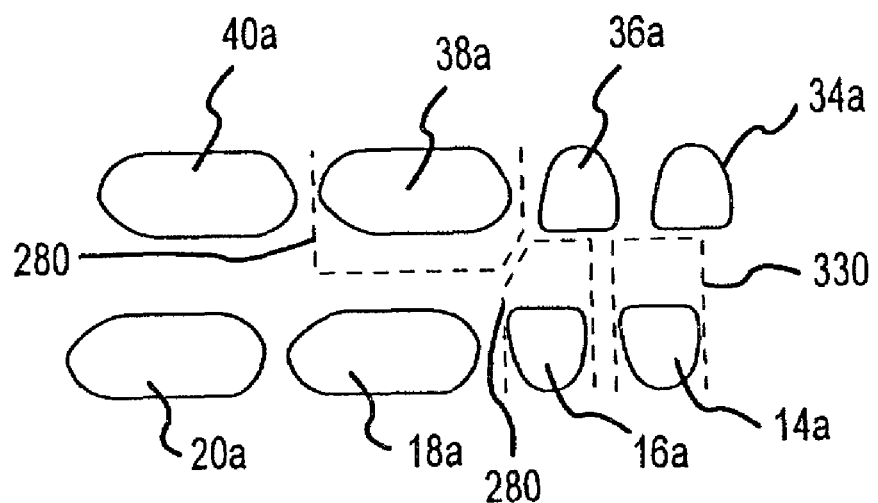
FIG. 27 is a cutaway side view of one side of upper and lower dental arches of a patient with another configuration of crown-based mandibular advancers and the crown of FIG. 25 for providing enhanced occlusal support.
Figure 28:
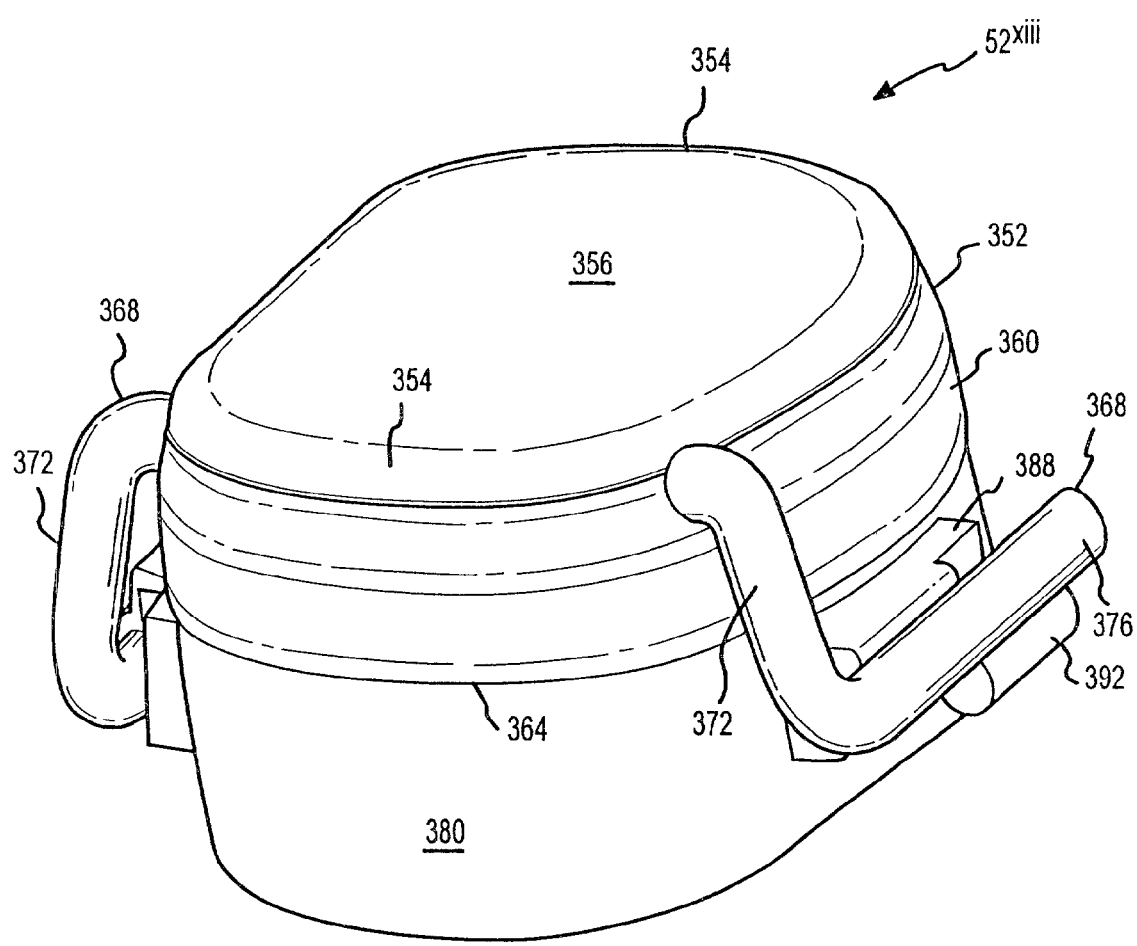
FIG. 28 is a perspective view of a cap/band mandibular advancer.
Figure 29:
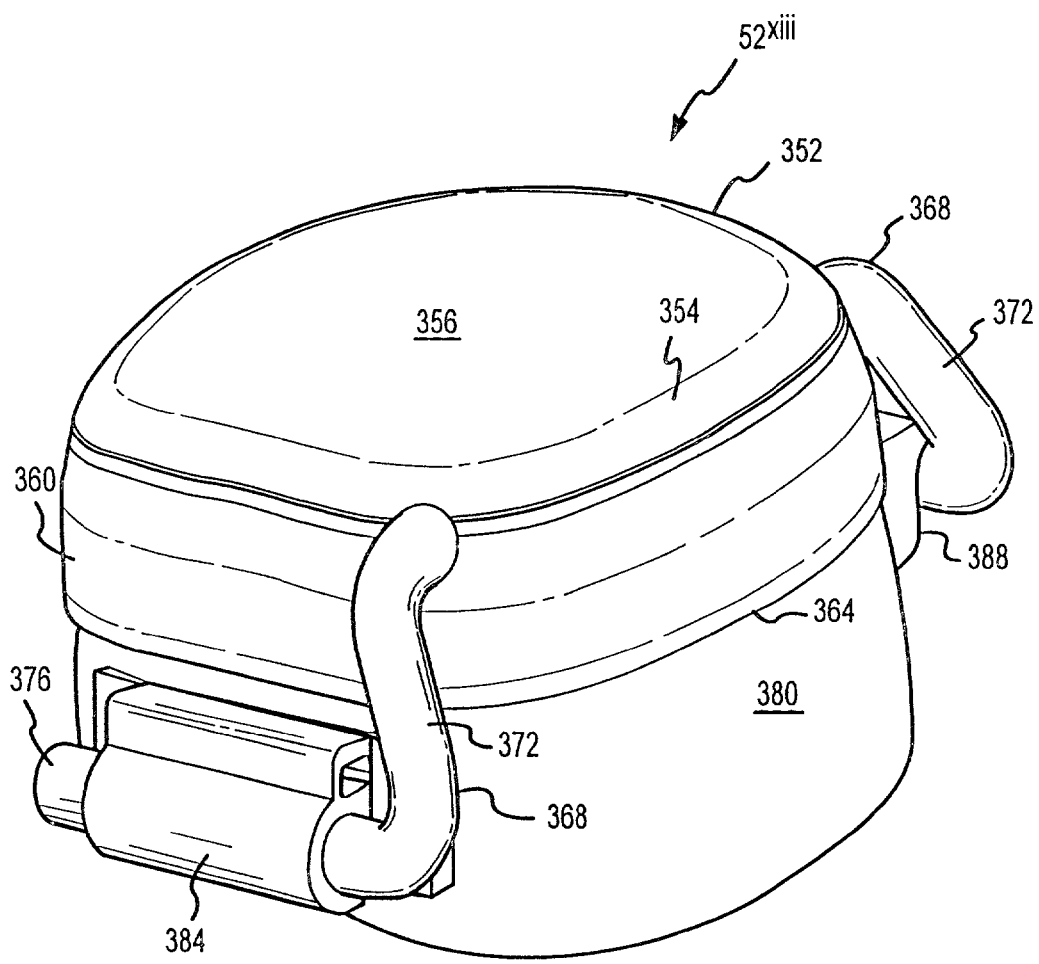
FIG. 29 is another perspective view of the cap/band mandibular advancer of FIG. 28.
Figure 30:
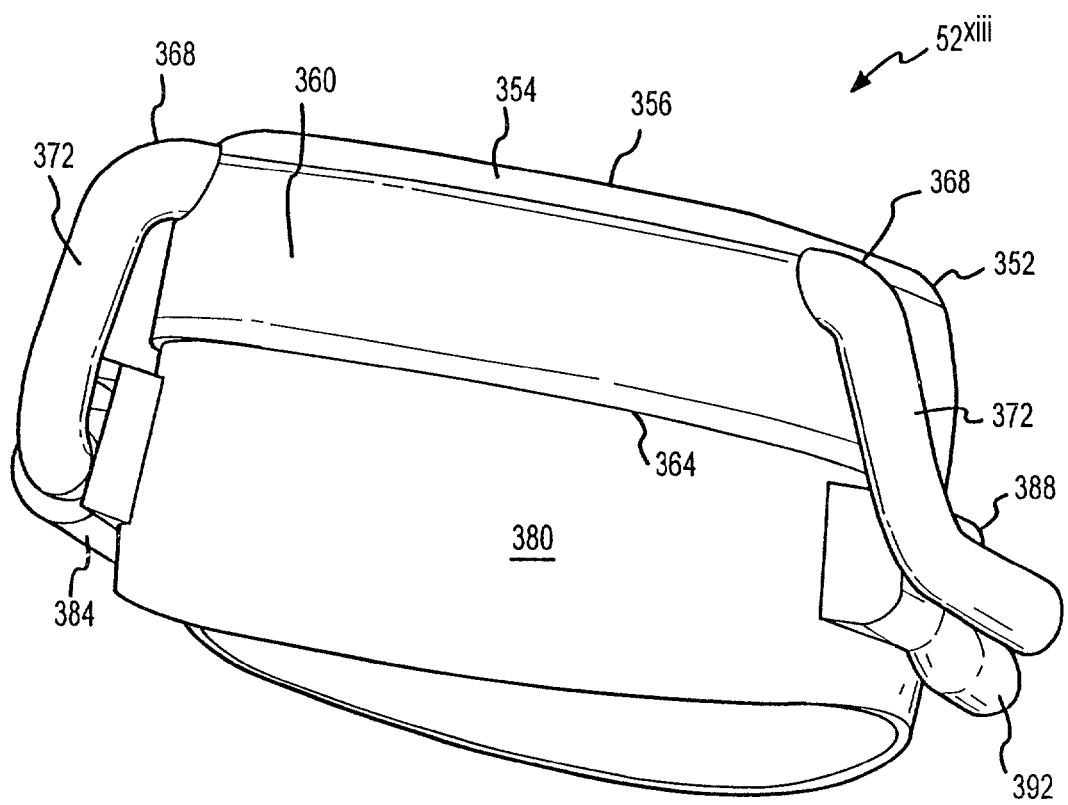
FIG. 30 is another perspective view of the cap/band mandibular advancer of FIG. 28.
Figure 31:
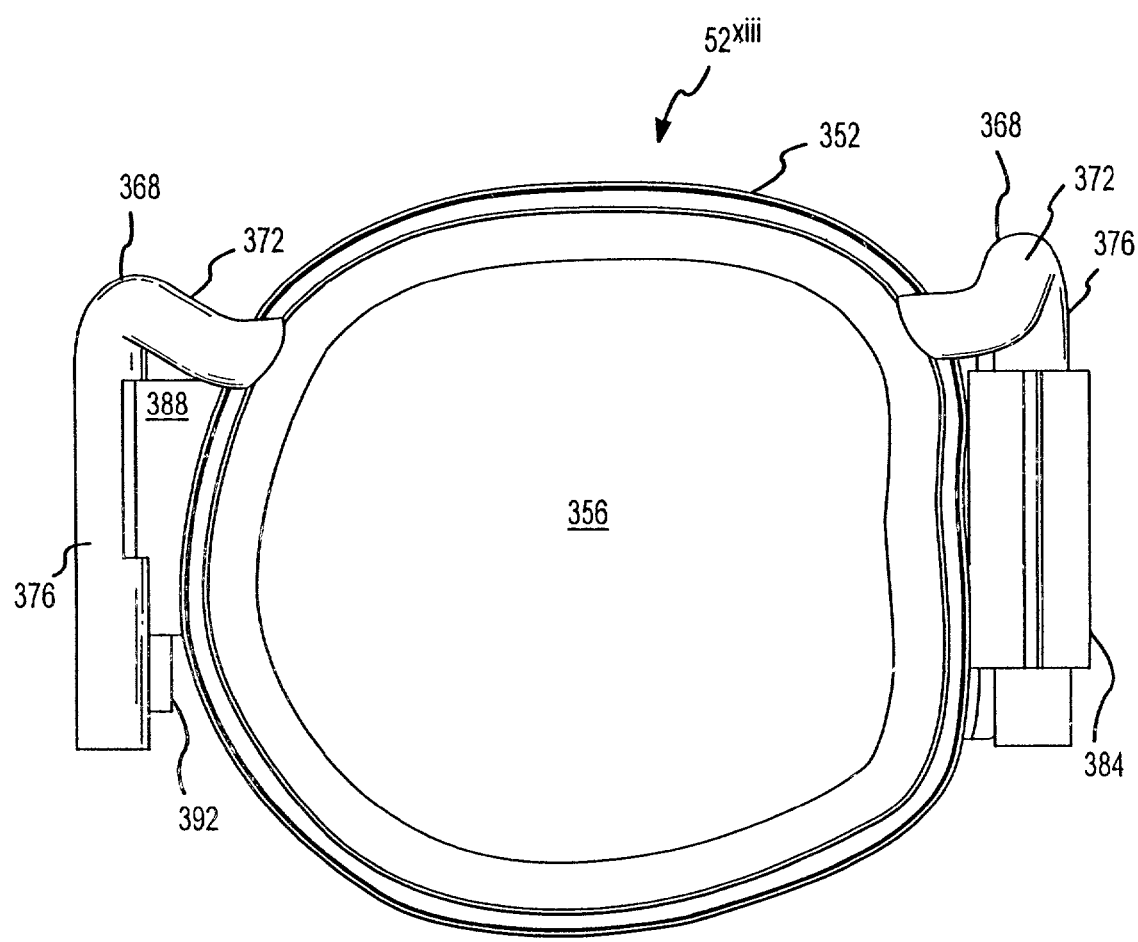
FIG. 31 is an occlusal view of the cap/band mandibular advancer of FIG. 28.

FIGS. 26 and 27 illustrate two examples of the "occlusal support" application/function for the crown 330 of FIG. 25. Typically it is desirable to have approximately ½ of the mesial-distal extent of the lower first molars 18 be actually oclussally-gingivally aligned with their corresponding upper second bicuspid 36 at the end of treatment. Both FIGS. 26 and 27 thereby illustrate the mandible 4 being in somewhat of a retracted position. FIG. 26 illustrates a situation where the patient's mandible 4 is disposed such that the upper first molars 38 are aligned with the lower first molars 18 (possibly at an intermediate time of treatment), whereas FIG. 27 illustrates a situation where the patient's mandible 4 is even in a more retracted state (possibly at the start of treatment). Both FIGS. 26 and 27 illustrate only one side of the patient's upper dental arch 26 and the patient's lower dental arch 6. It should be appreciated that the opposite side of each of these arches 26, 6 would be similarly configured with the devices which will now be described.

Mandibular advancement is affected in the FIG. 26 configuration by installing a crown 280 on the upper first molar 38a such that its crown mandibular advancement incline 292 is mesially disposed. Note the existence of the gap between the interior surface of the crown occlusal surface 284 and the occlusal surface of the upper first molar 38a. A crown 300 is installed on the lower first molar 18a such that its crown mandibular advancement incline 316 is at least generally mesially disposed. Note the existence of the gap between the interior surface of the first occlusal section 308 and the occlusal surface of the lower first molar 18a. Engagement of the opposing crown mandibular advancement inclines 292, 316 affects mandibular advancement at least generally in the above-described manner. In any case, a rather significant gap exists between the patient's upper dental arch 26 and lower dental arch 6 in the FIG. 26 configuration. Enhanced occlusal support for the patient in this condition is provided by installing one crown 330 of an enhanced occlusal-gingival extent on at least one of, and more preferably each of, the lower second bicuspid 16a (the "E" in the case of a younger patient) and the lower first bicuspid 14a (the "D" in the case of a younger patient) to provide a space between the occlusal surfaces of these teeth and the interior of the corresponding crown occlusal surface. These crowns 330 engage the upper second bicuspid 36a (the "E" in the case of a younger patient) and the upper first bicuspid 34a (the "D" in the case of a younger patient), typically when the crown occlusal surface 284 of the crown 280 engages the first occlusal section 308 of the crown 300. Similar benefits could be realized by installing one or more of such crowns 330 on an appropriate tooth of the upper dental arch 26 for interfacing with an opposing tooth on the lower dental arch 6.

Mandibular advancement is affected in the FIG. 27 configuration by installing a crown 280 on the upper first molar 38a such that its crown mandibular advancement incline 292 is mesially disposed. Note the existence of the gap between the interior of the crown occlusal surface 284 and the occlusal surface of the upper first molar 38a. Another crown 280 is installed on the lower second bicuspid 16a (the "E" in the case of a younger patient) such that its crown mandibular advancement incline 292 is distally disposed. Note the existence of the gap between the interior of the crown occlusal surface 284 and the occlusal surface of the lower second bicuspid 16a. Engagement of the opposing crown mandibular advancement inclines 292 affects mandibular advancement at least generally in the above-described manner. In any case, a rather significant gap exists between the patient's upper dental arch 26 and lower dental arch 6 in the FIG. 27 configuration. Enhanced occlusal support for the patient in this condition is provided by installing one crown 330 of an enhanced occlusal-gingival extent on the lower first bicuspid 14a to provide a space between the occlusal surface of the lower first bicuspid 14a and the interior of the crown occlusal surface 334. This crown 330 will engage the upper first bicuspid 34a, typically after/when the crown occlusal surfaces 284 of the opposing crowns 280 become engaged. Similar benefits again could be realized by installing one or more of such crowns 330 on an appropriate tooth of the upper dental arch 26 for interfacing with an opposing tooth on the lower dental arch 6.

Various types of mandibular advancers 52 have been described herein. A number of specific configurations of sorts for affecting mandibular treatment/therapy will now be addressed. In one embodiment, a crown 330 is mounted on each of the patient's upper first molars 38 such that a gap exists between the occlusal surface of the upper first molar 38 and the interior surface of the corresponding crown occlusal surface 334. A crown 330 is also mounted on each of the patient's lower second bicuspids 16 (the "E" in the case of a younger patient) such that a gap also exists between the occlusal surface of the lower second bicuspid 16 and the interior surface of the corresponding crown occlusal surface 334. Activation forces for affecting mandibular advancement are realized by engaging the transition region 342 on the mesial end of each of the crowns 330 mounted on the upper first molars 38 with the transition region 342 on the distal end of their corresponding crown 330 mounted on the lower second bicuspid 16.

Another configuration which may be utilized for mandibular advancement involves installing a crown 330 on each of the patient's upper first molars 38 such that a gap exists between the occlusal surface of the upper first molar 38 and the interior surface of the corresponding crown occlusal surface 334. A crown 300 is mounted on each of the patient's lower first molars 18 such that a gap exists between the occlusal surface of the lower first molars 18 and the interior surface of the corresponding crown occlusal surface 334, and further such that each second occlusal section 312 is mesially disposed. This configuration will typically be utilized for cases when the patient's mandible 4 is significantly retracted. In any case, activation forces for affecting mandibular advancement are realized by engaging the transition region 342 on the mesial end of each of the crowns 330 mounted on the upper first molars 38 with the crown mandibular advancement incline 316 of their corresponding crown 300 on the lower first molar 18.

Another configuration which may be utilized for mandibular advancement involves installing a crown 280 on each of the patient's upper first molars 38 such a gap exists between the occlusal surface of the upper first molar 38 and the interior surface of the corresponding crown occlusal surface 284, and further such that the crown mandibular advancement incline 292 is mesially disposed. A crown 280 is mounted on each of the lower second bicuspids 16 (the "E" in the case of a younger patient) such that a gap exists between the occlusal surface of the lower second bicuspid 16 and the interior surface of the corresponding crown occlusal surface 284, and further such that the crown mandibular advancement incline 292 is distally disposed. Activation forces for affecting mandibular advancement are realized by engaging the crown mandibular advancement incline 292 of the crowns 280 mounted on the upper first molars 38 with the crown mandibular advancement incline 292 of their corresponding crown 280 mounted on the lower second bicuspid 16.

Another configuration which may be utilized for mandibular advancement involves installing a crown 280 on each of the patient's upper first molars 38 such that a gap exists between the occlusal surface of the upper first molar 38 and the interior surface of the corresponding crown occlusal surface 284, and further such that the crown mandibular advancement incline 292 is mesially disposed. A crown 300 is mounted on each of the patient's lower first molars 18 such that a gap exists between the occlusal surface of the lower first molar 18 and the interior surface of the corresponding crown occlusal surface 304, and further such that the second occlusal section 312 is mesially disposed. Activation forces for affecting mandibular advancement are realized by engaging the crown mandibular advancement incline 292 of the crowns 280 mounted on the upper first molars 38 with the crown mandibular advancement incline 316 of their corresponding crown 300 mounted on the lower first molar 18.

Another configuration which maybe utilized for mandibular advancement involves installing a crown 280 on each of the patient's upper first molars 38 such that a gap exists between the occlusal surface of the upper first molar 38 and the interior surface of the corresponding crown occlusal surface 284, and further such that the crown mandibular advancement incline 292 is mesially disposed. A crown 330 is mounted on each of the patient's lower second bicuspids 16 (the "E" in the case of a younger patient) such that a gap also exists between the occlusal surface of the lower second bicuspid 16 and the interior surface of the corresponding crown occlusal surface 334. Activation forces for affecting mandibular advancement are realized by engaging the crown mandibular advancement incline 292 on the mesial end of each of the crowns 280 mounted on the upper first molars 38 with the transition region 342 on the distal end of their corresponding crown 330 mounted on the lower second bicuspid 16.

The crown 280 of FIGS. 21–22, the crown 300 of FIGS. 23–24, and the crown 330 of FIG. 25 have a number of features in common. Initially, these crowns 280, 300, and 330 are each seated on the subject tooth such that the crowns 280, 300, 330 cover at least substantially an entirety of the exposed enamel of the subject tooth (as will typically be the case for the crowns 102, 204, 176, and 252 as well). Typically, the gingival edge of the crowns 280, 300, 330 will at least extend to the gingiva of the patient, and will more typically actually extend about 1 mm to about 1.5 mm below or under the patient's gingiva. Another common feature is that each of these crowns 280, 300, and 330 are "taller" than conventional crowns or sit more "proudly" on a tooth when installed thereon in the above-noted manner. Stated another way, the crowns 280, 300, and 330 have an enhanced occlusal-gingival extent in comparison to conventional crowns. When each of these crowns 280, 300, and 330 are installed over the desired tooth in the desired dental arch, the enhanced occlusal-gingival extent provides a space between the occlusal surface of this underlying tooth and the interior of the relevant crown occlusal surface 284, 304, 3334. In one embodiment, the minimum vertical extent of this space is at least about 1.5 mm and is measured along an axis which is parallel with the tooth-long axis (which coincides with the axis about which the crown skirt 296, 320, 338 is formed). What is meant by the term "minimum vertical extent" is that the noted minimum vertical space exists between each point on the occlusal surface of the tooth and that portion of the relevant crown occlusal surface 284, 304, 334 which is disposed therebeyond along a reference axis which is parallel to the tooth-long axis of the subject tooth.

Another way of describing the above-noted space is to assume that you could move the crowns 280, 300, 330 gingivally (and parallel to the tooth-long axis) until it contacted an occlusal surface of its underlying tooth (the patient's gingiva obviously would not allow this much gingival travel). The noted space could then be defined by moving the crowns 280, 300, 330 occlusally (again parallel with the tooth-long axis) a distance of about 1.5 to about 2.0 mm, at which time the gingival extreme of the crowns 280, 300, 300 would be either disposed at the gingiva of the patient or this gingival extreme would be extending "below" or "under" the gingiva by the above-noted amount.

Those materials and manufacturing techniques described above in relation to the crown 102 of FIGS. 5–6 may be implemented for the crowns 280, 300, and 330. Moreover, those techniques which were discussed above with regarding to "fixing" or "attaching" any of the crowns 102, 140, 204, 176, 252 may be utilized for the crowns 280, 300, and 330 as well. In those cases where the crowns described herein are disposed in spaced relation to the occlusal surface of the underlying tooth, it may be advantages to have a rigid spacer occupy at least a portion of this space (e.g., by being embedded within the orthodontic bonding system material).

Another embodiment of a mandibular advancer 52 is illustrated in FIGS. 28–31. The mandibular advancer 52[xviii] includes a cap 352 which is disposed over the occlusal of an appropriate tooth and a band 380 which encircles this tooth. The 352 generally includes a cap occlusal surface 356 and a cap skirt 360. In the illustrated embodiment, the cap occlusal surface 356 is at least substantially flat or planar, and is preferably disposed at least generally parallel with the occlusal of the dental arch on which the 352 is installed. Alternatively, the cap occlusal surface 356 could be anatomically-shaped to at least generally approximate the occlusal surface of the tooth on which the cap 352 is installed (not shown). Unlike at least some of the embodiments discussed above which utilized crowns as mandibular advancers 52, the occlusal-gingival extent of the cap 352 is less than the occlusal-gingival extent of the tooth on which the same is mounted. Therefore, the gingival extreme 364 of the cap skirt 360 is occlusally-gingivally spaced from the patient's gingiva.

A pair of wires 368 are fixedly attached to the cap 352 on the buccal and lingual sides of the cap 352. These wires 368 each include a first section 372 which is at least generally occlusally-gingivally disposed, as well as a second section 376 which is at least generally mesial-distally disposed. A buccal tube 384 is fixedly attached to the band 380 on the buccal side thereof, while a catch 388 is fixedly attached to the band 380 on the lingual side thereof. A ligating tube 392 is also fixedly attached to the band 380 on the lingual side thereof. The ligating tube 392 is disposed gingivally of the catch 388. The second section 376 of one of the wires 368 is disposed within the buccal tube 384, while the second section 376 of the other wire 368 is disposed on the gingival side of the catch 388. The wire 368 which is disposed under the catch 388 maybe ligated to the band 380 via the ligating tube 392.

The band 380 is conventionally attached to tooth. The cap 352 may then be filled with a polymerizing material that is bonded to the interior of the cap 352 and disposed over the tooth and an annular occlusal portion of the band 380 (i.e., the cap 352 does not completely cover the band 380). At least at some point in time of the installation, one of the wires 368 is "slid" into the buccal tube 384 and the other wire 368 is disposed "under" the catch 388. Again, a ligature may further secure the wire 368 which is disposed "under" the catch 388 to the band 380 via the ligating tube 392. This interface between the cap 352 and the band 380 via the wires 368 may be sufficient in and of itself That is, the polymerizing material within the cap 352 (which cures into a shape which is in at least substantial conforming relation with the occlusal surface of the tooth) need not form a bond to the enamel of the tooth. In this case the mandibular advancer $52^{xiii}$ may then be configured as a removable appliance for repeated removal and installation by the practitioner or even the patient. In cases where the polymerizing material does bond the cap 352 to the tooth, the wires 368 may shelter or protect the bond from at least certain destructive forces which could otherwise cause this bond to fail. At a minimum the wires 368 function to align the cap 362 onto the tooth.

Forces for affecting movement of the mandible 4 using the mandibular advancer $52^{xiii}$ are realized by mounting the cap 352 in spaced relation to the occlusal surface of the tooth on which the cap 352 is mounted. The spacing discussed above in relation to the crowns 280, 300, and 330 is equally applicable to the cap 352. In any case, the cap 352 may assume a variety of configurations to provide an appropriate surface for affecting mandibular advancement forces. The configuration presented in FIGS. 28–31 is sufficient. A transition section 354 exists between the cap occlusal surface 356 and the cap skirt 360, which is of the same general shape/configuration as the transition 342 of the crown 330 of FIG. 25, and which is disposed on each of the mesial and distal ends of the cap 352. This transition section 354 may provide an appropriate surface for interfacing with another mandibular advancer 52 on the opposing dental arch to affect a desired movement of the mandible 4 in the same manner as the crown 330 of FIG. 25. The cap occlusal surface 356 and/or the occlusal portion of the cap skirt 360 could also be configured into the shape utilized by the crown 102 of FIGS. 5–6, the crown 176 of FIG. 16, the crown 252 of FIGS. 19–20B, the crown 280 of FIGS. 21–22, and the crown 300 of FIGS. 23–24 to also affect mandibular movement. It may also be possible to utilize the cap 352, alone but more likely in combination with the band 380 and the above-described interconnecting wires 368, to provide enhanced occlusal support in a manner similar to the crown 330 discussed above in relation to FIG. 25.

The various mandibular advancers 52 described herein provide a significant advance in one or more of the performance of the mandibular advancement technique, as well as in the assembly of such advancers 52. Although certain of the mandibular advancers 52 were described above in relation to a particular dental arch (i.e., the upper dental arch 26, the lower dental arch 6), each of the mandibular advancers 52 described herein may be used on both the lower dental arch 6 and on the upper dental arch 26. Moreover, although certain of the mandibular advancers 52 were positioned on the subject dental arch to affect mesial advancement of the mandible 4, each of the mandibular advancers 52 described herein may be installed on the lower arch 6 and/or the upper dental arch 26 to affect distal advancement of the mandible 4 (i.e., a retraction). Finally, any combination of the various mandibular advancers 52 described herein may be used on the same side of the lower dental arch 6 and the upper dental arch to affect advancement of the mandible 4.

It should also be appreciated that the mandibular advancers 52 described herein may benefit from the use of other appliances or armamentarium in conjunction therewith. For instance, it may be desirable to provide a buccal hook on each side of both the patient's upper dental arch 26 and lower dental arch 6 so that elastics may be utilized to facilitate engagement of the opposing mandibular advancers 52 (e.g., one elastic which interconnects the upper dental arch 26 and lower dental arch 6 on one side thereof, and another elastic which interconnects the upper dental arch 26 and lower dental arch 6 on the opposite side thereof). In certain cases, these hooks may be directly attached to the buccal of the mandibular advancer 52 itself (e.g., when formed from metal).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A mandibular advancement system, comprising:
   a cap comprising a cap occlusal surface, a cap skirt, and an active surface for mandibular advancement, wherein said cap is disposable over a single first tooth of a patient;
   a band disposable about the first tooth of the patient, whereby said cap and band are installed on the same first tooth, and wherein said cap skirt is disposed over an annular, occlusally-disposed portion of said band so as to have an annular, gingivally-disposed portion of said band exposed;
   a first wire attached to a lingual side of an exterior of said cap and interconnected with a lingual side of said band on said gingivally-disposed portion of said band; and
   a second wire attached to a buccal side of an exterior of said cap and interconnected with a buccal side of said band on said gingivally-disposed portion of said band.

2. A system, as claimed in claim 1, wherein:
   an occlusal-gingival extent of said cap is less than an occlusal-gingival extent of the first tooth of the patient, whereby a gingival edge of said cap is disposed in spaced relation to the patient's gingiva.

3. A system, as claimed in claim 1, wherein:
   said active surface comprises a mandibular advancement incline.

4. A system, as claimed in claim 1, wherein:
   said active surface comprises a transition surface between said cap occlusal surface and said cap skirt.

5. A system, as claimed in claim 4, wherein:
   said transition surface is convex.

6. A system, as claimed in claim 4, wherein:
said active surface in the form of said transition surface is disposed on both the mesial and distal of said cap.

7. A system, as claimed in claim 1, wherein:
said band comprises a mesio-distally extending buccal tube disposed on and attached to said buccal side of said band on said gingivally-disposed portion of said band, wherein said second wire is disposed within said buccal tube.

8. A system, as claimed in claim 1, wherein:
said band comprises a catch disposed on and attached to said lingual side of said band on said gingivally-disposed portion of said band, wherein said first wire is disposed on a gingival side of said catch, and wherein said catch fails to encircle any portion of said first wire.

9. A system, as claimed in claim 8, wherein:
said band further comprises a ligating tube attached to said lingual side of said band on said gingivally-disposed portion of said band.

10. A system, as claimed in claim 9, wherein:
a ligature wire may be used to secure said first wire on said gingival side of said catch.

11. A system, as claimed in claim 9, wherein:
said ligating tube is disposed gingivally of said catch, and wherein said first wire is disposed at an intermediate elevation between said catch and said ligating tube.

12. A system, as claimed in claim 1, wherein:
said band comprises a mesio-distally extending buccal tube disposed on and attached to said buccal side of said band, wherein said second wire is disposed within said buccal tube; and
said band comprises a catch disposed on and attached to said lingual side of said band, wherein said first wire is disposed on a gingival side said catch, and wherein said catch fails to encircle any portion of said first wire.

13. A system, as claimed in claim 1, wherein:
said band comprises a mesio-distally extending buccal tube disposed on and attached to said buccal side of said band, wherein said second wire is disposed within said buccal tube;
said band comprises a catch disposed on and attached to said lingual side of said band, wherein said first wire is disposed on a gingival side said catch, and wherein said catch fails to encircle any portion of said first wire; and
said band further comprises a ligating tube attached to said lingual side of said band.

14. A system, as claimed in claim 13, wherein:
a ligature wire may be used to secure said first wire on said gingival side of said catch.

15. A system, as claimed in claim 13, wherein:
said ligating tube is disposed gingivally of said catch, and wherein said first wire is disposed at an intermediate elevation between said catch and said ligating tube.

16. A system, as claimed in claim 1, wherein:
said first and second wires both comprise a first section that is at least generally occlusally-gingivally disposed, as well as a second section and is at least generally mesial-distally disposed, wherein said second sections are gingivally disposed relative to their corresponding said first section and interface with said band.

17. A mandibular advancement system, comprising:
a cap comprising a cap occlusal surface, a cap skirt, and an active surface for mandibular advancement, wherein said cap is disposable over a patient's tooth, wherein said active surface comprises a transition surface between said cap occlusal surface and said cap skirt, and wherein said transition surface is convex;
a band disposable about the patient's tooth;
a first wire attached to a lingual side of said cap and interconnected with a lingual side of said band; and
a second wire attached to a buccal side of said cap and interconnected with a buccal side of said band.

18. A mandibular advancement system, comprising:
a cap comprising a cap occlusal surface, a cap skirt, and an active surface for mandibular advancement, wherein said cap is disposable over a patient's tooth, wherein said active surface comprises a transition surface between said cap occlusal surface and said cap skirt, and wherein said active surface in the form of said transition surface is disposed on both the mesial and distal of said cap;
a band disposable about the patient's tooth;
a first wire attached to a lingual side of said cap and interconnected with a lingual side of said band; and
a second wire attached to a buccal side of said cap and interconnected with a buccal side of said band.

19. A mandibular advancement system, comprising:
a cap comprising a cap occlusal surface, an annular cap skirt, and an active surface for mandibular advancement, wherein said cap is disposable over a patient's tooth;
an annular band disposable about the patient's tooth, whereby said cap and band are disposable on the same tooth;
a first wire attached to a lingual side of an exterior of said cap and interconnected with a lingual side of said band; and
a second wire attached to a buccal side of an exterior of said cap and interconnected with a buccal side of said band, wherein said band comprises a mesio-distally extending buccal tube disposed on and fixedly attached to said buccal side of said band, wherein said second wire of said cap is disposed within said buccal tube, wherein said band further comprises a catch disposed on and fixedly attached to said lingual side of said band, wherein said first wire of said cap is disposed on a gingival side said catch, and wherein said catch fails to encircle any portion of said first wire.

20. A system, as claimed in claim 19, wherein:
an occlusal-gingival extent of said cap is less than an occlusal-gingival extent of the patient's tooth, whereby a gingival edge of said cap is disposed in spaced relation to the patient's gingiva.

21. A system, as claimed in claim 19, wherein:
said active surface comprises a mandibular advancement incline.

22. A system, as claimed in claim 19, wherein:
said active surface comprises a transition surface between said cap occlusal surface and said cap skirt.

23. A system, as claimed in claim 19, wherein:
said transition surface is convex.

24. A system, as claimed in claim 22, wherein:
said active surface in the form of said transition surface is disposed on both the mesial and distal of said cap.

25. A system, as claimed in claim 19, wherein:
said cap skirt is disposed over an annular, occlusally-disposed portion of said band so as to have an annular, gingivally-disposed portion of said band exposed.

26. A system, as claimed in claim 19, wherein:
said band further comprises a ligating tube attached to said lingual side of said band.

27. A system, as claimed in claim 26, wherein:
a ligature wire may be used to secure said first wire on said gingival side of said catch.

28. A system, as claimed in claim 26, wherein:
said ligating tube is disposed gingivally of said catch, and wherein said first wire is disposed at an intermediate elevation between said catch and said ligating tube.

29. A system, as claimed in claim 19, wherein:
said first and second wires both comprise a first section that is at least generally occlusally-gingivally disposed, as well as a second section and is at least generally mesial-distally disposed, wherein said second sections are gingivally disposed relative to their corresponding said first section and interface with said band.

\* \* \* \* \*